(12) United States Patent
Rodríguez Herrero et al.

(10) Patent No.: US 12,635,940 B2
(45) Date of Patent: May 26, 2026

(54) CLOSED-LOOP DRUG INFUSION SYSTEM WITH SYNERGIC CONTROL

(71) Applicants: UNIVERSIDAD POLITÉCNICA DE MADRID, Madrid (ES); FUNDACIÓN PARA LA INVESTIGACIÓN E INNOVACIÓN BIOMÉDICA DEL HOSPITAL UNIVERSITARIO INFANTA LEONOR Y DEL HOSPITAL UNIVERSITARIO DEL SURESTE, Madrid (ES)

(72) Inventors: Agustin Rodríguez Herrero, Madrid (ES); Victor Pimentel Naranjo, Madrid (ES); María Elena Hernando Pérez, Madrid (ES); José María Calvo Vecino, Madrid (ES); Alfredo Abad Gurumeta, Madrid (ES)

(73) Assignees: UNIVERSIDAD POLITÉCNICA DE MADRID FUNDACION PARA LA INVESTIGACIÓN E INNOVACIÓN BIOMÉDICA, Madrid (ES); DEL HOSPITAL UNIVERSITARIO INFANTA LEONOR Y, Madrid (ES)

( * ) Notice: Subject to any disclaimer, the term of this patent is extended or adjusted under 35 U.S.C. 154(b) by 690 days.

(21) Appl. No.: 17/996,968

(22) PCT Filed: Apr. 23, 2021

(86) PCT No.: PCT/ES2021/070273
§ 371 (c)(1),
(2) Date: Oct. 24, 2022

(87) PCT Pub. No.: WO2021/214368
PCT Pub. Date: Oct. 28, 2021

(65) Prior Publication Data
US 2023/0355171 A1 Nov. 9, 2023

(30) Foreign Application Priority Data

Apr. 23, 2020 (ES) ............................... ES202030337

(51) Int. Cl.
*A61B 5/00* (2006.01)
*A61M 5/14* (2006.01)
(Continued)

(52) U.S. Cl.
CPC .......... *A61B 5/4839* (2013.01); *A61B 5/4821* (2013.01); *A61M 5/1408* (2013.01);
(Continued)

(58) Field of Classification Search
CPC ............... A61B 5/4821; A61B 5/4839; A61M 2005/14208; A61M 5/16827; A61M 5/1723; G16H 20/17; G16H 40/60
See application file for complete search history.

(56) References Cited

U.S. PATENT DOCUMENTS

2012/0095437 A1* 4/2012 Hemmerling ....... A61M 5/1723
604/503

FOREIGN PATENT DOCUMENTS

| EP | 1704819 A2 * | 9/2006 | ........... A61B 5/4076 |
| ES | 2483596 A2 | 8/2014 | |
| WO | 2010043054 A1 | 4/2010 | |

OTHER PUBLICATIONS

Heusden, et al.; "Robust MISO Control of Propofol-Remifentanil Anesthesia Guided by the NeuroSENSE Monitor"; IEEE Transactions on Control Systems Technology, vol. 26, No. 5, Sep. 2018; pp. 1758-1770.
(Continued)

*Primary Examiner* — Deanna K Hall
(74) *Attorney, Agent, or Firm* — Jayne Saydah

(57) ABSTRACT

A system automatically calculates drug infusion applicable to a patient to induce a satisfactory anesthetic state during
(Continued)

surgery. The automatic calculation system would be determined by target values of physiological monitors to evaluate the patient's condition. Automatic infusion increases patient safety, reducing post-surgical morbidity and mortality, and reduces continuous decision-making by the specialist. An electronic system implements a MIMO-PID controller that calculates the infusion of various drugs on the basis of a control error defined by deviations in the patient's condition, which is analyzed by several monitors. The automatic drug infusions are determined by safety systems for preventing under and/or over infusion events and are complemented with correction and feedback systems.

10 Claims, 4 Drawing Sheets

(51) Int. Cl.
| | |
|---|---|
| *A61M 5/168* | (2006.01) |
| *A61M 5/172* | (2006.01) |
| *G16H 20/17* | (2018.01) |
| *A61M 5/142* | (2006.01) |

(52) U.S. Cl.
CPC ...... *A61M 5/16827* (2013.01); *A61M 5/1723* (2013.01); *G16H 20/17* (2018.01); *A61M 2005/14208* (2013.01); *A61M 2205/50* (2013.01)

(56) References Cited

OTHER PUBLICATIONS

International Search Report dated Sep. 6, 2021 issued in PCT/ES2021/070273.

Kuck, et al.; "The Three Laws of Autonomous and Closed-Loop Systems in Anesthesia"; Anesthesia and Analgesia; Feb. 2017, vol. 124, No. 2; pp. 377-380.
Liu, et al.; "Closed-Loop Coadministration of Propofol and Remifentanil Guided by Bispectral Index: A Randomized Multicenter Study"; International Society for Anaesthetic Pharmacology; Mar. 2011 • vol. 112 • No. 3; pp. 546-557.
Merigo, et al.; A model-based control scheme for depth of hypnosis in anesthesia; Biomedical Signal Processing and Control 42 (2018) 216-229.
Merigo, et al.; "Event Based Control of Propofol and Remifentanil Coadministration During Clinical Anesthesia"; 2017; 3 pages.
Merigo, et al.; "Optimized PID control of propofol and remifentanil coadministration for general anesthesia"; Commun Nonlinear Sci Numer Simulat 72 (2019) 194-212.
Miranda, et al.; "Optimal time for constant drug infusion initialization in neuromuscular blockade control"; 2014 IEEE International Symposium on Medicalmeasurements and Applications (MEMEA) 2014; p. 258-263.
Nieuwenhuyzen et al.; "Target-Controlled Infusion Systems—Role in Anaesthesia and Analgesia"; Clin Pharmacokinet Feb. 2000; 38 (2): 181-190.
Padula, et al.; "Optimized PID control of depth of hypnosis in anesthesia"; Computer Methods and Programs in Biomedicine 144 (2017) 21-35.
Pawlowski, et al.; "Two-degree-of-freedom control scheme for depth of hypnosis in anesthesia"; Preprints of the 3rd IFAC Conference on Advances in Proportional-Integral-Derivative Control, Ghent, Belgium, May 9-11, 2018; 6 pages.
Peters, et al.; "Dual-hormone artificial pancreas: benefits and limitations compared with single-hormone systems"; DIABETICMedicine; pp. 450-459.
Schneider, et al.; "Detection of awareness in surgical patients with EEG-based indicesÐbispectral index and patient state index"; British Journal of Anaesthesia 91 (3): 329-335 (2003).
Written Opinion dated Jun. 14, 2021 issued in PCT/ES2021/070273.

* cited by examiner k: control error    j: monitor    i: drug
12: BIS           1: BIS        1: PPF
13: NOX           2: NOX        2: RMF
14: NMB           3: NMB        3: RCN

CLOSED-LOOP DRUG INFUSION SYSTEM WITH SYNERGIC CONTROL

CROSS-REFERENCE

This is a 371 Application of International Application No. PCTES2021070273 filed Apr. 23, 2021, which claims priority to Spanish application No. P202030337 filed Apr. 23, 2020. The disclosures of the prior applications are hereby incorporated by reference herein in their entirety.

BACKGROUND OF THE INVENTION

Field of the Invention

The present invention is framed in the field of closed-loop (CL) control for the automatic infusion of drugs, for example in anesthesia administered intravenously (IV), using for this purpose a bank of control algorithms based on variants of the PID (proportional-integral-derivative) controller.

The present invention belongs to the field of automatic control of biological systems and its main field of application is the automated multicontrol of IV drug infusions in anesthetic acts. However, it can be used in the control of acute or chronic diseases in which the patient requires multiple monitoring with the infusion of several drugs. A direct application of this invention would be its use in an artificial pancreas for the control of type 1 diabetes with glucose monitoring and with the continuous exogenous infusion of insulin and glucagon (Peters, T. M., and A. Haidar. "Dual-hormone artificial pancreas: benefits and limitations compared with single-hormone systems." *Diabetic Medicine* 35.4 (2018): 450-459).

Similarly and under the same concept, it can be applied in the veterinary field for the simultaneous dispensing of various drugs to animals, in order to apply anesthesia thereto. It could also be used to control acute or chronic pathologies in which it is necessary to monitor physiological variables of the animal and to administer drugs simultaneously.

BACKGROUND OF THE INVENTION

According to the American Board of Anesthesiology, anesthesiology is the branch of medicine that provides insensitivity to pain during surgical, obstetric, therapeutic and diagnostic procedures. Anesthesiologists administer drugs by different access modes to the human body so as to establish a state in which non-traumatic surgery can be performed for the patient.

The current techniques of general anesthesia establish three main objectives that must be met: 1) Depth of Hypnosis (DoH); 2) Analgesia (ANG); and 3) Muscle Relaxation (MRX). There are methods for estimating these variables (in this description these variables are referred to as monitors), respectively: 1) the bispectral index (BIS) is an empirically derived multifactorial electroencephalogram measure, whose given index correlates with the patient's DoH (G. Schneider et al., Detection of awareness in surgical patients with eeg-based indexes, bispectral Index and patient State Index, *British journal of anaesthesia* 91 (3) (2003) 329-335); 2) the nociceptive stimulation response index (NOX) is a single-variant index calculated from the weighted concentrations of the drug used, proposed to predict the probability of response to a nociceptive stimulus during anesthesia (P. Schumacher et al. Time-based, online display of a noxious stimulus response index based on pharmacological data, in: Annual Meeting of the American Society of Anesthesiologists. San Francisco, California. *Anesthesiology, Vol. 107,* 2007, p. A17); and 3) the muscle relaxant is administered in order to maintain the desired level of neuromuscular blockade (NMB) during surgery (A. Miranda et al., Optimal time for constant drug infusion initialization in neuromuscular blockade control, in: 2014 IEEE International Symposium on Medical Measurements and Applications (MeMeA), *IEEE,* 2014, pp. 1-6). Additionally, there are other physiological variables subject to monitoring and of great interest to the specialist such as cardiography, blood pressure, blood oxygenation or capnography.

The process of general IV anesthesia, generally known as total IV anesthesia, takes place in a clinical scenario that generally presents itself in three phases: 1) Induction phase (IPh), in which the drugs are administered by bolus and constant infusion; the patient is led to the desired anesthetic state, trying to obtain the desired values of DoH, ANG and MRX as quickly as possible; 2) Maintenance phase (MPh), in which the surgical procedure begins, and an infusion of different drugs conveniently modified by the anesthesiologist is performed to maintain the desired anesthetic state; the drugs used simultaneously can present a synergistic effect; the objective in this phase is to maintain the anesthetic state close to the target values; and 3) Recovery phase (RPh), in which the administration of the drugs is stopped to recover consciousness, to eliminate ANG and MRX (F. Padula, C. Ionescu, N. Latronico, M. Paltenghi, A. Visioli, G. Vivacqua, Optimized PID control of depth of hypnosis in anesthesia, *Computer and methods in biomedicine* 144-35) (2017) 21-35).

Currently, the most used protocols in IV are the manually controlled infusions and the Target Control Infusion (TCI) method, which consists of administering a constant infusion of the drugs also during the MPh, properly calculated from a desired reference value of infusion (A Miranda et al., Optimal time for constant drug infusion initialization in neuromuscular blockade control, in: 2014 IEEE International Symposium on Medical Measurements and Applications (MeMeA), *IEEE,* 2014, pp. 1-6). The administration of IV drugs by infusion offers multiple advantages (M. C. van den Nieuwenhuyzen et al., Burm Target-controlled infusion systems, *Clinical pharmacokinetics* 38 (2) (2000) 181-190). However, several factors do not make the use of TCI so clear in clinical practice, such as the experience of the anesthetist, personal preference, interindividual pharmacokinetic clinical variability and understanding of the principles of TCI. As a result, TCI has become the bridge between ongoing research and current clinical practice, opening the possibility of designing sophisticated automation systems.

The application of control with feedback on the infusion drugs in anesthesia has been extensively investigated since the automatic control in CL presents a series of socioeconomic advantages, such as: 1) the reduction of costs for both the patient and the health system, as well as the reduction of the workload of the anesthesiologist; 2) the reduction of the dose used, which implies a faster recovery time and, consequently, a better postoperative recovery of the patient; and 3) a more robust performance with less episodes of over/underdosing. In summary, this translates into greater clinical safety for the patient (F. Padula et al., Optimized PID control of depth of hypnosis in anesthesia, *Computer methods and programs in biomedicine* 144 (2017) 21-35). However, although foggy systems have been developed in recent decades, all of them remain prototypes without CE marking or FDA approval for clinical use.

The automatic control in anesthesia aims to maintain a satisfactory anesthetic state close to the target values of the desired monitoring variables in addition to a high rejection of the disturbances considered as the modifications in the anesthetic state caused by the surgeon's action (F. Padula et al, Optimized PID control of depth of hypnosis in anesthesia, *Computer methods and programs in biomedicine* 144 (2017) 21-35).

Kai Kuck, in his article "The Three Laws of Autonomous and Closed-Loop Systems in anaesthesia" (Kuck, K., & Johnson, K. B. The three laws of autonomous and closed-loop systems in anesthesia. *Anesthesia & Analgesia* 124 (2017) 377-380), postulates three laws to which autonomous anesthesia systems must be subject: 1) do no harm, the system must be safe for the patient and in case of failure, it must fail slightly, ruling out any type of danger; 2) be transparent, that is, the system must execute the established objectives in a reliable and understandable way, allowing the anesthesiologist to predict its behavior; and 3) reduce the workload, the system itself must not require excessive attention to maintain an adequate function, allowing the anesthesiologist to focus on other more important tasks.

The most common control algorithms used in CL in anesthesia are: Internal control model, predictive control model, proportional integral and derivative control (PID) and artificial intelligence-based control (F. Padula et al, Optimized PID control of depth of hypnosis in anesthesia, *Computer methods and programs in biomedicine* 144 (2017) 21-35). Even so, the most effective option remains PID control, the subject of recent and diverse proposals. In addition, it has been shown that the performance achieved by a properly adjusted PID controller applied in anesthesia, has the same or better performance than any other controller, regardless of its complexity (L. Merigo et al, Event based control of propofol and remifentanil coadministration during clinical anesthesia, in: 2017 3rd International Conference on Event-Based Control, *Communication and Signal Processing, IEEE,* 2017, pp. 1-8).

PID controllers have been used through different design approaches to address the problem of automation of the anesthetic act. There are primary proposals for bis-guided coadministration of PPFs and RMFs. (N. Liu et al., Closed-loop coadministration of propofol and remifentanil guided by bispectral Index: a randomized multicenter study, *Anesthesia & Analgesia* 112 (3) (2011) 546-557), but a more complex design approach is also presented (K. van Heusden et al., Robust miso control of propofol-remifentanil anesthesia guided by the neurosense monitor, *IEEE Transactions on Control Systems Technology* 26 (5) (2018) 1758-1770), offering a multi-input single output (MISO) controller for PPF-RMF anesthesia guided by feedback from a DoH measurement.

Other approaches based on PID controllers have been implemented to regulate DoH in anesthesia using the administration of PPF and BIS as a controlled variable, with the difference that Padula and his team (F. Padula et al., Optimized PID control of depth of hypnosis in anesthesia, *Computer methods and programs in biomedicine* 144 (2017) 21-35) establish a set of twelve virtual patients (VPs) representative of a relatively large population variance that is used to test the robustness of the controller; and Mengo (L. Merigo et al., Event based control of propofol and remifentanil coadministration during clinical anesthesia, in: 2017 3rd International Conference on Event-Based Control, Communication and Signal Processing (EBCCSP) *IEEE,* 2017, pp. 1-8) proposes a new event generator with high noise filtering properties, in addition to a PIDPIus controller, where the control action is updated only when an event occurs. Finally, Merigo and his team (L. Merigo et al., A model-based control scheme for depth of hypnosis in anesthesia, *Biomedical Signal Processing and Control* 42 (2018) 216-229) performed a PID control algorithm based on the patient's pharmacokinetic and pharmacodynamic model for the administration of PPF, whose estimated concentration at the place of effect is used as a feedback signal.

Some of the more recent works offer different architectures for PID control schemes, such as Pawlowskl and its team (A. Pawlowski et al, Two-degree of-freedom control scheme for depth of hypnosis in anesthesia, *IFACPapersOn-Line* 51 (4) (2018) 72-77), which present a PID with two degrees of freedom for DoH, using BIS as a controlled variable. They have two low-pass filters, one of first order and one of second order, to obtain an adequate response to the changes produced in the reference signal. Another notable approach is the one presented recently by Merigo (L Merigo et al., Optimized pid control of propofol and remifentanil coadministration for general anesthesia, *Communications in Nonlinear Science and Numerical Simulation* 72 (2019) 194-212), where a PID-based CL-optimized system for DoH is proposed using PPF-RMF and BIS. In this work, the tuning has been carried out by applying PSO (Particle Swarm Optimization) to a cohort of 13 VPs.

A series of difficulties related to the problems in the control in CL of the anesthetic act that must be addressed has been identified: 1) unilateral control, due to the non-consideration of antagonist drugs; 2) delays, oscillations in CL and instabilities increase because of delays; 3) the variables to be controlled are not the variables coming from the monitors (the measurements); 4) the drugs have a memory effect when administered to the patient; and 5) the synergy that the different drugs to be administered can present. In addition, in the prior art certain limitations have been detected in the application of CL control in anesthesia, namely: 1) there is no formal proposal that combines the main anesthetic states (DoH, ANG and MRX); and 2) although PID-based algorithms are effective in solving the control problem, it has not been used in a multivariable way for the infusion of multiple drugs using multiple physiological variables.

In connection with the present invention, the following prior art documents have been found:

ES2297940T3 (2001), Apparatus for providing a conscious patient with relief from pain and anxiety associated with medical or surgical procedures. A system is claimed to provide, through a conservative management of computer software, the delivery of one or more amnesic, analgesic or sedative drugs with the electronic monitoring of one or more physiological conditions of the patient.

CN1561241B (2002), Apparatuses and methods for titrating drug delivery. A drug delivery system to a patient is claimed, wherein said system comprises: a user interface for receiving user information, a drug delivery device, and a physiological monitor regulated by an algorithm.

U.S. Pat. No. 8,998,808B2 (2004), System for identifying patient response to anesthesian infusion. An apparatus for assisting a practitioner during administration of an anesthetic drug to a patient is claimed, comprising: a processing system receiving the corresponding data, a memory storing the data, a processor resolving the formula, and a screen displaying the resulting data to the anesthesiologist.

ES2293366T3 (2006), Computer-Controlled Intravenous Drug Delivery System. An apparatus for controlling

5 and directing an IV anesthesia and/or the application of other IV drugs to a patient is claimed. In addition, it stores the data of the expert benefiting from the system, which being recoverable.

ES2267767 (2007), System and method of adaptive drug delivery. A System for determining and maintaining a desired drug concentration level in a patient for determining and maintaining a desired effect on that patient is claimed. The system comprises a sensor assembly, a drug delivery unit, and a CL delivery controller with an input coupled to said assembly and an output coupled to said delivery unit.

JP5792629B2 (2009), System for controlling the means for injection of anesthetic or sedative agents. An IV anesthesia control system for the induction and maintenance of sedation is claimed, which contains the means for the acquisition and analysis of the control signal.

ES2429688 (2013), Apparatuses and methods for titrating drug delivery. A System for providing drug delivery to a patient is claimed. Said System comprises a user interface, a drug delivery device, a plurality of physiological monitors and a processor that integrates the user interface.

CN103212119B (2013), Based on target-controlled infusion pump bis anesthesia feedback controller. A bis-based closed loop control system containing a fuzzy PID control algorithm is claimed.

CN106859592A (2015), TCI-based (target controlled infusion-based) anesthesia depth intelligent control system. An intelligent TCI control system based on the monitoring of BIS in anesthesia is claimed.

US20180296759A1 (2016), Methods and Systems for closed-loop control of drug administration. A closed loop control system is claimed for the administration of at least one drug to a patient, the control system containing: an actuator that administers the drug, one or more physiological monitors, and a processor that determines the control signal.

With reference to the above, there are inventions that claim control systems based on a single monitor, specifically BIS (CN103212119B and CN106859592A); others, among the different main anesthetic states refer only to sedation (JP5792629B2). One of the most advanced patents claims a system for the infusion of at least one drug based on one or more physiological monitors; however, said invention bases its control on the use of a Model Predictive Controller (MPC) in which there is also no reference to the synergy that the drugs used can present.

There is no indication that there is currently a system of infusion pumps that integrates the method of multi-infusion of anesthetic drugs with MIMO-PID control applied in IV anesthetic acts, configurable to the number of drugs used, to the number of monitoring variables that are used and that considers the synergistic relationship between the different drugs used. Additionally, there is no indication of a method that contemplates the multi-infusion of other types of drugs in addition to those used in anesthesia.

BRIEF SUMMARY OF THE INVENTION

To help understand the method, which is executed by an electronic system, lists of names and their meaning of abbreviations, variables, and systems are initially presented.

The abbreviations simplify long names that appear very frequently in the text, with this list aiding the comprehension of the text until readers become familiar with the concepts (when an acronym refers to a plural name it will end with "s", for example "IV" refers to intravenous as an adjective and "IVs" refers to multiple intravenous acts). Below are the abbreviations in alphabetical order:

| Abbreviation | Meaning |
| --- | --- |
| ANG | Analgesia |
| CL | Closed loop |
| D | Derivative |
| DoH | Depth of Hypnosis |
| eBIS | Bispectral index or equivalent hypnosis monitor |
| eNMB | Neuromuscular Blockade Index or equivalent muscle relaxation monitor |
| eNOX | Noxious Stimulation Response Index or equivalent nociception monitor |
| ePPF | Propofol or equivalent drug with hypnotic properties |
| eRCN | Rocuronium or equivalent drug with muscle-blockade properties |
| eRMF | Remifentanil or equivalent drug with analgesic properties |
| I | Integral |
| IPh | Induction phase |
| IV | Intravenous |
| MIMO-PID | Multiple Input and Multiple Output PID Controller System |
| MISO-PID | Multiple Input/Single Output PID Controller System |
| MPh | Maintenance phase |
| MRX | Muscle relaxation |
| OL | Open loop |
| P | Proportional |
| PID | Proportional, Integral and Derivative Controller System |
| RPh | Recovery phase |
| SISO-PID | Single Input and Single Output PID Controller |
| SynPID | MIMO-PID Driver with Synergy |

The list of variables is intended for the reader to become familiar with their names quickly and easily, defining concepts and their location in the figures. The variables referenced in bold and in [brackets] define matrices, those referenced only in bold define column vectors (a transposition is performed to facilitate their writing and interpretation), and those referenced in italics and not in bold define scalar variables. The most important ones are listed below according to the order of appearance in the description:

| Name | Definition of the variable |
| --- | --- |
| y | monitoring variables vector (6) |
| $y_1$ | eBIS monitor (6.1) |
| $y_2$ | eNOX Monitor (6.2) |
| $y_3$ | eNMB Monitor (6.3) |
| $u_{pt}$ | Anesthetic Drug Continuous Infusion Vector (5) |
| $u_{pt1}$ | Continuous infusion of the ePPF (5.1) |
| $u_{pt2}$ | Continuous infusion of the eRMF (5.2) |
| $u_{pt3}$ | Continuous infusion of the eRCN (5.3) |
| $d_{sur}$ | Vector of surgical actions (7) |
| $u_{ol}$ | Manual protocol infusion vector (4) |
| $u_{ol1}$ | Manual infusion of the ePPF (4.1) |
| $u_{ol2}$ | Manual infusion of the eRMF (4.2) |
| $u_{ol3}$ | Manual infusion of the eRCN (4.3) |
| d | Manual bolus vector at startup |
| $d_1$ | EPPF manual bolus |
| $d_2$ | ERMF manual bolus |
| $d_3$ | ERCN manual bolus |
| D | Vector containing the boluses per unit of induction mass |
| $D_1$ | ePPF dose |
| $D_2$ | eRMF dose |
| $D_3$ | eRCN dose |
| $r_{ol}$ | IPh infusion Vector |
| $r_{ol1}$ | Induction infusion of ePPF |
| $r_{ol2}$ | Induction infusion of eRMF |
| $r_{ol3}$ | Induction infusion of eRCN |
| R | Constant infusion vector in IPh |

| Name | Definition of the variable |
| --- | --- |
| $R_1$ | Constant infusion of ePPF |
| $R_2$ | Constant infusion of eRMF |
| $R_3$ | Constant infusion of eRCN |
| P | Infusion decrease in Mph vector |
| $P_1$ | Decreased ePPF infusion |
| $P_2$ | Decreased eRMF infusion |
| $P_3$ | Decreased eRCN infusion |
| W | Patient Weight |
| $y_T$ | Target of monitored variables vector (8) |
| $y_{T1}$ | Target of eBIS (8.1) |
| $y_{T2}$ | Target of eNOX (8.2) |
| $y_{T3}$ | Target of eNMB (8.3) |
| $y_f$ | filtered monitoring variables vector (10) |
| $y_{f1}$ | EBIS filtering (10.1) |
| $y_{f2}$ | eNOX filtering (10.2) |
| $y_{f3}$ | eNMB filtering (10.3) |
| $f_c$ | Cut-off frequency vector |
| $f_1$ | eBIS filter cut-off frequency |
| $f_2$ | eNOX filter cut-off frequency |
| $f_3$ | eNMB filter cut-off frequency |
| N | PID filtering coefficient |
| $e_1$ | eBIS control error vector (12) |
| $e_{p1}$ | proportional eBIS (12.1) |
| $e_{I1}$ | Integral eBIS (12.2) |
| $e_{D1}$ | derivative eBIS |
| $e_{F1}$ | filtered derivative eBIS (12.3) |
| $e_2$ | eNOX control error vector (13) |
| $e_{p2}$ | proportional eNOX (13.1) |
| $e_{I2}$ | integral eNOX (13.2) |
| $e_{D2}$ | derivative eNOX |
| $e_{F2}$ | filtered derivative eNOX (13.3) |
| $e_3$ | eNMB control error vector (14) |
| $e_{P3}$ | proportional eNMB (14.1) |
| $e_{I3}$ | integral eNMB (14.2) |
| $e_{D3}$ | derivative eNMB |
| $e_{F3}$ | filtered derivative eNMB (14.3) |
| $e_P$ | Proportional asymmetric error vector |
| $e_{p1}$ | proportional eBIS (12.1) |
| $e_{p2}$ | proportional eNOX (13.1) |
| $e_{P3}$ | proportional eNMB (14.1) |
| $e_I$ | Integral symmetric error vector |
| $e_{I1}$ | Integral eBIS (12.2) |
| $e_{I2}$ | integral eNOX (13.2) |
| $e_{I3}$ | integral eNMB (14.2) |
| $e_D$ | Derivative asymmetric error vector |
| $e_{D1}$ | derivative eBIS |
| $e_{D2}$ | derivative eNOX |
| $e_{D3}$ | derivative eNMB |
| $e_F$ | Filtered derivative asymmetric error vector |
| $e_{F1}$ | filtered derivative eBIS (12.3) |
| $e_{F2}$ | filtered derivative eNOX (13.3) |
| $e_{F3}$ | filtered derivative eNMB (14.3) |
| [B] | Asymmetry matrix in proportional action |
| $\beta$ | Asymmetry vector in proportional action |
| $\beta_{11}$ | eBIS weighting |
| $\beta_{22}$ | eNOX Weighting |
| $\beta_{33}$ | eNMB weighting |
| $y_{thb}$ | Vector of thresholds that determine the maximum value of p |
| $y_{thb1}$ | eBIS threshold $\beta$ |
| $y_{thb2}$ | eNOX threshold $\beta$ |
| $y_{thb3}$ | eNMB threshold $\beta$ |
| [G] | Asymmetry matrix in derivative action |
| $\gamma$ | Asymmetry vector in derivative action |
| $\gamma_{11}$ | eBIS weighting |
| $\gamma_{22}$ | eNOX Weighting |
| $\gamma_{33}$ | eNMB weighting |
| $y_{thg}$ | Vector of thresholds that determine the maximum value of y |
| $y_{thg1}$ | eBIS threshold $\gamma$ |
| $y_{thg2}$ | eNOX threshold $\gamma$ |
| $y_{thg3}$ | eNMB threshold $\gamma$ |
| $u_{pid}$ | Vector of control infusions (15) |
| $u_1$ | ePPF control infusion (15.1) |
| $u_2$ | eRMF control infusion (15.2) |
| $u_3$ | eRCN control infusion (15.3) |
| $[K_P]$ | Proportional gains matrix |
| $K_P$ | Direct proportional gains vector |
| $K_{Pi}$ | Direct proportional gains relative to drug vector/ |

| Name | Definition of the variable |
| --- | --- |
| $K_{Pij}$ | Proportional gain relative to monitor j and drug/ |
| $[K_I]$ | Comprehensive gains matrix |
| $K_I$ | Direct integral gains vector |
| $K_{Ii}$ | Integral gains relative to drug vector/ |
| $K_{Iij}$ | Integral gain relative to monitor j and to drug j and monitor j |
| $[T_I]$ | Integral action times matrix |
| $T_I$ | Vector of direct integral action times |
| $T_{Ii}$ | Vector of integral action times relative to drug/ |
| $T_{Iij}$ | Integral action time relative to monitor j and drug/ |
| $[K_D]$ | Derivative gains matrix |
| $K_D$ | Direct derivative gains vector |
| $K_{Di}$ | Direct derivative gains vector relative to drug/ |
| $K_{Dij}$ | Derivative gain relative to monitor j and to drug/ |
| $[T_D]$ | Derivative action time matrix |
| $T_D$ | Direct derivative action time vector |
| $T_{Di}$ | Derivative action time vector relative to drug/ |
| $T_{Dij}$ | Derivative action time relative to monitor j and to drug/ |
| [SYN] | Drug synergy matrix |
| $S_i$ | Synergy vector related to drug/ |
| $S_{ij}$ | Synergy relative to controller $C_{ij}$ |
| $K_{ol}$ | Gains vector on infusion vector of manual protocol |
| $K_{ol1}$ | Gain modulating infusion of manual protocol relative to ePPF |
| $K_{ol2}$ | Gain that modulates the infusion of the manual protocol relative to the eRMF |
| $K_{ol3}$ | Gain that modulates the infusion of the manual protocol relative to the eRCN |
| $u_{cr}$ | Correction vector (18) |
| $u_{cr1}$ | Corrective infusion of ePPF (18.1) |
| $u_{cr2}$ | Corrective infusion of eRMF (18.2) |
| $u_{cr3}$ | Corrective infusion of ePPF (18.3) |
| $y_{Lo}$ | Correction activation lower thresholds vector |
| $L_1$ | Lower threshold relative to eBIS |
| $L_2$ | Lower threshold relative to eNOX |
| $L_3$ | Lower threshold relative to eNMB |
| $Y_{HI}$ | Correction activation upper threshold vector |
| $H_1$ | Upper threshold relative to eBIS |
| $H_2$ | Upper threshold relative to eNOX |
| $H_3$ | Upper threshold relative to eNMB |
| $u_{Sf}$ | Reliable control vector (20) |
| $u_{sf1}$ | Reliable infusion of ePPF (20.1) |
| $u_{sf2}$ | Reliable infusion of eRMF (20.2) |
| $u_{sf3}$ | Reliable infusion of eRCN (20.3) |
| $u_{LO}$ | Drug infusion lower limit vector |
| $u_{L1}$ | Lower limit relative to ePPF |
| $u_{L2}$ | Lower limit relative to eRMF |
| $u_{L3}$ | Lower limit relative to eRCN |
| $U_{HI}$ | Drug infusion upper limit vector |
| $U_{H1}$ | Upper limit relative to ePPF |
| $U_{H2}$ | Upper limit relative to eRMF |
| $U_{H3}$ | Upper limit relative to eRCN |
| Ucl | Automatic infusions vector (22) |
| $U_{cl1}$ | Automatic infusion of ePPF (22.1) |
| $U_{cl2}$ | Automatic infusion of eRMF (22.2) |
| $U_{cl3}$ | Automatic infusion of eRCN (22.3) |
| $u_{mn}$ | Continuous infusion pump system resolution vector |
| $u_{mn1}$ | ePPF pump resolution |
| $u_{mn2}$ | eRMF pump resolution |
| $u_{mn3}$ | eRCN pump resolution |
| $t_i$ | IPh Start Time |
| $t_m$ | Mph start time |
| $t_r$ | RPh Start Time |
| $T_s$ | Method execution time |
| $[\ ]^T$ | Transposition of vectors and matrices |

The list of systems is meant to provide their quick and easy location in the figures and in the description. Below, they are listed according to the order of appearance in the description:

| System | Subsystem |
|---|---|
| (1) patient | |
| (2) infusion pump system | (2.1) hypnotic drug infusion pump (ePPF) |
| | (2.2) analgesic drug infusion pump (eRMF) |
| | (2.3) relaxant drug infusion pump (eRCN) |
| (3) monitoring equipment | (3.1) DOH monitor (eBIS) |
| | (3.2) ANG monitor (eNOX) |
| | (3.3) MRX monitor (eNMB) |
| (24) synergistic multi-PID control system (SynPID) | |
| (9) filter bank | (9.1) hypnosis filter |
| | (9.2) nociception filter |
| | (9.3) muscle relaxation filter |
| (11) control error generator | 28: DoH error generator |
| | 29: ANG error generator |
| | 30: MRX error generator |
| (16) multivariable controller | with MIMO-PID synergy, denoted by the matrix [PID] |
| (25) MISO-PID-ePPF control subsystem, denoted by vector $C_1$ | (25.1) SISO-PID eBIS-ePPF, denoted by variable $C_{11}$ |
| | (25.2) SISO-PID eNOX-ePPF, denoted by variable $C_{i2}$ |
| | (25.3) SISO-PID eNMB-ePPF, denoted by variable $C_{i3}$ |
| (26) MISO-PID-eRMF control subsystem, denoted by vector $C_2$ | (26.1) SISO-PID eBIS-eRMF, denoted by variable $C_{2}i$ |
| | (26.2) SISO-PID eNOX-eRMF, denoted by variable $C_{22}$ |
| | (26.3) SISO-PID eNMB-eRMF, denoted by variable $C_{23}$ |
| (27) MISO-PID-eNMB control subsystem, denoted by vector $C_3$ | (27.1) SISO-PID eBIS-eRCN, denoted by variable $C_{3i}$ |
| | (27.2) SISO-PID eNOX-eRCN, denoted by variable $C_{32}$ |
| | (27.3) SISO-PID eNMB-eRCN, denoted by variable $C_{33}$ |
| (17) correction system | (17.1) ePPF infusion corrective subsystem |
| | (17.2) eRMF infusion corrective subsystem |
| | (17.3) eRCN infusion corrective subsystem |
| (19) security system | (19.1) ePPF infusion safety subsystem |
| | (19.2) eRMF infusion safety subsystem |
| | (19.3) eRCN infusion safety subsystem |
| (21) quantification system | (21.1) ePPF infusion quantifier subsystem |
| | (21.2) eRMF infusion quantifier subsystem |
| | (21.3) eRCN infusion quantifier subsystem |
| (23) switching system | |

The present invention relates to a system for the automatic multi-infusion of synergistic drugs to patients by IV, comprising:

an infusion pump subsystem (2), configured to deliver to the patient (1) a number of drugs;

a monitoring subsystem (3), configured to measure a set of physiological variables with patient status information;

a control subsystem (24), configured to adapt the amount delivered of each drug (5) by the infusion pump subsystem (2), based on a predetermined initial infusion amount (4), monitoring target values (8), a feedback (6) of the measured physiological variables and a synergy between the drugs, wherein the control subsystem comprises:

a control error generating module (11) configured to calculate errors (12, 13, 14) based on the monitoring target values (8) and the feedback of the measured physiological variables;

a controller (16) configured to determine a control infusion (15) for each of the drugs based on the errors (12, 13, 14) calculated by the control error generating module (11) and the predetermined initial infusion amount (4);

a correction module (17) configured to receive the measurements of the set of physiological variables from the monitoring subsystem (3) and modify the control infusion (15) of the controller (16), increasing said infusion as a function of an upper threshold or decreasing it as a function of a lower threshold, to set the physiological variables at a preset safe range for the physiological variables; and a safety module (19) configured to receive the control infusion (15) of each drug and modify said infusion by limiting it between two infusion values, a lower limit and an upper limit, which ensure that there is no excess medication for each drug, allowing to work with the physiological variables in a safe range.

Additionally, overdosage or underdosage protection modules are contemplated in the control subsystem with the safety (19) and correction (17) modules configured to maintain the drug infusion at safe values.

One of the embodiments of the invention discloses a multi-infusion system of anesthetic drugs with synergy by means of control by CL MIMO-PID (SynPID) applied in anesthetic acts via IV; this system is multidimensional and configurable to the number of drugs used and to the number of monitoring variables that are used. The system is implemented on an electronic device, where the following steps are executed:

step 1—obtaining a monitoring variables vector for hypnosis (DoH), analgesia (ANG) and muscle relaxation (MRX); additionally, other monitoring variables can be used. From now on these are referred to as the monitoring variables vector (6), which can be BIS, NOX and NMB or other equivalent monitors denoted as eBIS, eNOX and eNMB, of the DoH, ANG and MRX, respectively. The value of the monitoring variables vector (6) depends mainly on the infusion of drugs with hypnotic, analgesic and/or muscle-blocking properties, such as propofol (PPF), remifentanil (RMF) and rocuronium (RCN), although equivalent drugs can be used denoted as ePPF, eRMF and eRCN; in addition, other anesthetic drugs can be used. These drugs are henceforth referred to as drugs or anesthetic drugs that are infused into the patient via IV; these make up the anesthetic drug infusion vector (5). The anesthetic drug infusion vector (5) is administered to the patient (1) via an infusion pump system (2). The monitoring equipment (3) gather the effects of the anesthetic drugs on the patient (1) and the surgical actions vector (7) those of the surgeon in an intervention;

step 2—calculating the anesthetic drug infusion vector (5) for the anesthetic drugs considered, by means of a MIMO-PID control system with synergy (SynPlD) (24) according to the monitoring variable vector (6), the manual protocol infusion vector (4) and the target vector of the monitored variables (8);

step 3,—clearing noise and artifacts from the monitoring variables vector (6) by a filter bank (9) to obtain a filtered monitoring variables vector (10);

step 4.—calculating the control error vectors (12, 13, 14) by means of a control error generator (11) from the filtered monitoring variables vector (10) and the monitored variables target vector (8); in particular this consists of calculating the control error vector of the eBIS monitor (12) by means of a DoH error generator (28) from the hypnosis filtered monitoring by means of the eBIS monitor (10.1) and its target value (8.1); calculating the control error vector of the eNOX monitor (13) by means of an ANG error generator (29) from the ANG filtered monitoring by means of the eNOX monitor (10.2) and its target value (8.2); calculating the control error vector of the eNMB monitor (14) by means of an RMX error generator (30) from the MRX filtered monitoring by means of the eNMB monitor (10.3) and its target value (8.3);

step 5—calculating a control infusion vector (15) by means of a multivariable controller with synergy MIMO-PID (16), composed of three MISO-PID control subsystems (25, 26, 27) based on the control error vectors (12, 13, 14) and on the manual protocol infusion vector (4). Each PID control infusion is formed by the sum of a proportional infusion, an integral infusion and a derivative infusion.

step 6,—calculating a correction vector (18) by means of an infusion correction system (17) from the filtered monitoring variables vector (10);

step 7,—calculating a reliable control vector (20) by means of a safety system (19) from the control infusion vector (15) and the correction vector (18);

step 8,—calculating an automatic infusion vector (22) by a quantifying system (21) based on the reliable control vector (20);

step 9,—defining the anesthetic drug infusion vector (5) applied to the patient (1) by a switching system (23) from the manual protocol infusion vector (4) and the automatic infusion vector (22) calculated by the SynPlD control system (24);

step 10,—calculating the control infusion of the ePPF drug (15.1) by means of a MISO-PID-ePPF control subsystem (25) composed of three SISO-PID controllers (25.1, 25.2, 25.3) that relate the infusion of the ePPF drug to the control error vectors (12, 13, 14);

step 11,—calculating the control infusion of the eRMF drug (15.2) by means of a MISO-PID-eRMF control subsystem (26) composed of three SISO-PID controllers (26.1,26.2, 26.3) that relate the infusion of the eRMF drug to the control error vectors (12, 13, 14);

step 12,—calculating the control infusion of the eRCN drug (15.3) by means of a MISO-PID-eNMB control subsystem (27) composed of three SISO-PID controllers (27.1,27.2, 27.3) that relate the infusion of the eRCN drug to the control error vectors (12, 13, 14).

The system of multi-infusion of anesthetic drugs with synergy by control in CL MIMO-PID applied in anesthetic acts via IV is called the SynPlD control system. The SynPlD needs different types of information to obtain the anesthetic drug infusion vector (5) on patients, below are the actions and calculations that must be done in each step described above.

Step 2) executed by the SynPlD control system further comprises acquiring the Information:

2.1.—Measuring the monitoring variables vector (6), $$y=[y_1 y_2 \ldots y_r]^T \qquad [2.1]$$

Where y is the monitoring variables vector (6); $y_1$ is the eBIS monitor; $y_2$ is the eNOX monitor; $y_3$ is the eNMB monitor and the rest of the vector components from $y_4$ to $y_r$ are other possible monitor incorporations. The superscript T stands for vector transposition.

2.2.—Defining the manual protocol infusion vector (4) known as open-loop manual medical protocol (OP), $$u_{o1}=[u_{o l1} u_{o l2} \ldots u_{o ls}]^T, \qquad [2.2]$$

Where $u_{o1}$ is the manual protocol infusion vector (4); $u_0 n$ is the infusion of the manual protocol for the ePPF; $u_{0l2}$ is the infusion of the manual protocol for the eRMF; $u_{0l3}$ is the infusion of the manual protocol for the eRCN and the other components of the vector from $u_{0l4}$ to $u_{0ls}$ are other possible decisions of other drugs incorporated into the system.

2.3.—Calculate the manual protocol infusion vector (4) in OP, $$u_{o1}(t)=d(t_i)+r_{o1}(t), \qquad [2.3]$$

2.3.1.—Where d is the manual boluses vector at the time of starting IPh at time $t_i$, $$d(t_i) = \frac{D \cdot W}{T_s}, \qquad [2.4]$$

$$D = [D_1 \quad D_2 \quad \ldots \quad D_s]^T,$$

Where D is the vector containing the boluses per unit mass of each drug; I/I/ is the weight of the patient and $T_s$ is the execution period.

2.3.2.—Where rot is the infusion vector of anesthetic drugs in IPh, $$r_{o1}(t) = \begin{cases} R \cdot W, & t_i \le t < t_m \\ R \cdot W - P \cdot (t - t_m), & t_m \le t < t_r \end{cases}, \qquad [2.5]$$

$$R=[R_1 R_2 \ldots R_s]^T,$$

$$P=[P_1 P_2 \ldots P_s]^T,$$

Where R is the constant infusion vector in IPh, from $t_i$ when the IPh begins to tR when the MPh of anesthesia begins; P is the vector of the decrease of infusion in MPh; and W is the patient's weight.

2.4.—Setting the monitored variables target vector (8), $$y_T=[y_{T1} y_{T2} y_{Tr}]^T, \qquad [2.6]$$

Where $y_f$ is the monitored variables target vector (8); $y_{f1}$ is the target on the eBIS monitor; $yf_2$ is the target on the eNOX monitor; $yf_3$ is the target on the eNMB monitor and the other vector components from $yf_4$ to $yf_r$ are other possible targets on new monitor incorporations to the method.

Step 3) executed in the SynPID control system further comprises a filter bank (9) for:

3.1.—Calculating the filtered monitoring variables vector (10), $$y_f = [y_{f1} y_{f2} \ldots y_{fr}]^T, \qquad [3.1]$$

Where $y_f$ is the filtered monitoring variables vector; $y_{f1}$ is the filtering of the eBIS monitor; $y_{f2}$ is the filtering of the eNOX monitor; $y_{f3}$ is the filtering of the eNMB monitor and the rest of the vector components from $y_{f4}$ to $y_{fr}$ are the filtering of new monitor incorporations to the system.

3.2.—Defining a filter bank (9), based on low-pass filters of order iv, $$H(f) = \frac{Y_f(f)}{Y(f)} = \frac{1}{\left(1 + \frac{j \cdot f}{f_c}\right)^{n_H}}, \qquad [3.2]$$

Where $y$ is the monitoring variables vector (6); $y_f$ is the filtered monitoring variables vector (10); $n_H$ is the order of the filter; G is the cut-off frequency vector of the filter bank (9) given by $$f_c = [f_1 f_2 \ldots f_r]^T, \qquad [3.3]$$

Where $f_c$ is the cut-off frequency vector; $f_1$ is the cut-off frequency of the eBIS filter; $f_2$ is the cut-off frequency of the eNOX filter; $f_3$ is the cut-off frequency of the eNMB filter and the other components of the vector from $f_4$ to $f_r$ are the cut-off frequencies of the cleaning system on new filter incorporations to the system.

The vector G is calculated by the equation $$f_c = \frac{N}{T_D}, \qquad [3.4]$$

Where N is the filtering coefficient PID and $T_D$ is the vector of direct derivative action times.

Step 4) executed in the SynPID control system further comprises a control error generator (11) for:

4.1.—Calculating an eBIS $e_1$ monitor control error vector (12) with the DoH error generator (28), an eNOX $e_2$ monitor control error vector (13) with the ANG error generator (29), and an eNMB $e_3$ monitor control error vector (14) with the RMX error generator (30), each with its proportional, integral, and derivative components (12.1, 12.2, 12.3), (13.1, 13.2, 13.3), and (14.1, 14.2, 14.3). The corresponding errors from $e_4$ to $e_r$ are those related to the new monitors incorporated into the control system, $$e_1 = [e_{P1} \ e_{I1} \ e_{F1}]^T \qquad [4.1]$$
$$e_2 = [e_{P2} \ e_{I2} \ e_{F2}]^T,$$
$$\ldots$$
$$e_r = [e_{Pr} \ e_{Ir} \ e_{Fr}]^T$$

Where $e_{Pj}$ refers to the proportional asymmetric error of the PID; $e_{ij}$ refers to the integral symmetric error of the PID; $e_{Fj}$ refers to the filtered derivative error of the PID; and j refers to an integer between 1 and r referring to the monitored variable.

4.2.—Calculating the asymmetric proportional, symmetric integral and asymmetric derivative errors of each SISO-PID controller, using the $y_f$ filtered monitoring variables vector (10) and the $y_\tau$ monitored variables target vector (8), $$e_P = -B \cdot y_T + y_f = [e_{P1} \ e_{P2} \ \ldots \ e_{Pr}]^T \qquad [4.2]$$

$$e_I = -I \cdot y_T + y_f = [e_{I1} \ e_{I2} \ \ldots \ e_{Ir}]^T$$

$$e_D = -G \cdot y_T + y_f = [e_{D1} \ e_{D2} \ \ldots \ e_{Dr}]^T,$$

$$e_F = e_D - \frac{T_D}{N} \frac{de_f}{dt} = [e_{F1} \ e_{F2} \ \ldots \ e_{Fr}]^T$$

Where $y_\tau$ is the vector of the monitored variables targets (8); $y_f$ is the vector of the filtered monitoring variables (10); I is the identity matrix; $T_D$ is the vector of direct derivative action times and N is the filtering coefficient PID.

4.2.1.—[B] is the matrix with the influence of the "weighting set point" in the proportional action of the PIDs, also known as the asymmetry in the proportional error, $$[B] = \begin{bmatrix} \beta_{11} & 0 & \cdots & 0 \\ 0 & \beta_{22} & \cdots & 0 \\ \vdots & \vdots & \ddots & \vdots \\ 0 & 0 & \cdots & \beta_{rr} \end{bmatrix}, \qquad [4.3]$$

$$\beta = \mathrm{diag}([B])$$

Where $\beta_{jj}$ is the weight on the target of the proportional action j, $$\beta = \begin{cases} \dfrac{-y_f - y_{thb}}{y_T - y_{thb}} + 2, & y_f < y_T \\ 1, & y_f \geq y_T \end{cases}, \qquad [4.4]$$

Where $y_{thb}$ is a vector of thresholds that determine the maximum value of $\beta$.

4.2.2.—G is the matrix with the influence of the "weighting set point" on the derivative action of the PIDs; it is also known as the asymmetry in the derivative error, $$[G] = \begin{bmatrix} \gamma_{11} & 0 & \cdots & 0 \\ 0 & \gamma_{22} & \cdots & 0 \\ \vdots & \vdots & \ddots & \vdots \\ 0 & 0 & \cdots & \gamma_{rr} \end{bmatrix}, \qquad [4.5]$$

$$\gamma = \mathrm{diag}([G])$$

Where $\gamma_{jj}$ is the weight on the target of the derivative action j, $$\gamma = \begin{cases} \dfrac{-y_f - y_{thg}}{y_T - y_{thg}} + 2, & y_f < y_T \\ 1, & y_f \geq y_T \end{cases} \qquad [4.6]$$

Where $y_{thg}$ is a vector of thresholds that determine the maximum value of $\gamma$.

4.3.—Calculating the control error vector of the eBIS monitor (12) by means of a DoH error generator (28) from the filtered DoH monitoring by means of the eBIS monitor (10.1) and its target value (8.1), $$\begin{aligned} e_{P1} &= -\beta_{11} \cdot y_{T1} + y_{f1} \\ e_{I1} &= -y_{T1} + y_{f1} \\ e_{D1} &= -\gamma_{11} \cdot y_{T1} + y_{f1} \;, \\ e_{F1} &= e_{D1} - \frac{T_{D11}}{N} \frac{de_{F1}}{dt} \end{aligned} \qquad [4.7]$$

4.4.—Calculating the control error of the eNOX monitor (13) using an ANG error generator (29) from the filtered monitoring of the ANG using the eNOX monitor (10.2) and its target value (8.2), $$\begin{aligned} e_{P2} &= -\beta_{22} \cdot y_{T2} + y_{f2} \\ e_{I2} &= -y_{T2} + y_{f2} \\ e_{D2} &= -\gamma_{22} \cdot y_{T2} + y_{f2} \;, \\ e_{F2} &= e_{D2} - \frac{T_{D22}}{N} \frac{de_{F2}}{dt} \end{aligned} \qquad [4.8]$$

4.5.—Calculating the control error vector of the eNMB monitor (14) using an MRX error generator (30) from the filtered monitoring of the RMX using the eNMB monitor (10.3) and its target value (8.3), $$\begin{aligned} e_{P3} &= -\beta_{33} \cdot y_{T3} + y_{f3} \\ e_{I3} &= -y_{T3} + y_{f3} \\ e_{D3} &= -\gamma_{33} \cdot y_{T3} + y_{f3} \;, \\ e_{F3} &= e_{D3} - \frac{T_{D33}}{N} \frac{de_{F3}}{dt} \end{aligned} \qquad [4.9]$$

Step 5) executed by the SynPlD control system further comprises a MIMO-PID synergistic and multivariable controller (16) for:

5.1.—Defining the control infusions vector (15), $$u_{pid} = [u_1 u_2 \ldots u_s]^T, \qquad [5.1]$$

Where $u_1$ is the control infusion of the ePPF (15.1); $u_2$ is the control infusion of the eRMF (15.2); $u_3$ is the control infusion of the eRCN (15.3) and $u_4$ to $u_s$ are the infusions of new drugs that can be incorporated in the control system.

5.2.—Calculating the control infusion vector (15) using a MIMO-PID synergistic and multivariable controller (16), the control error vectors of the eBIS (12), eNOX (13) and eNMB (14) monitors and the manual protocol infusion vector (4), $$u_{pid} = [PID] \cdot [SYN] + K_{ol} \cdot u_{ol}, \qquad [5.2]$$

Where:

5.2.1.—[PID] is the matrix of SISO-PID controllers that make up the MIMO-PID synergistic and multivariable controller (16), $$[PID] = \begin{bmatrix} C_{11} & C_{12} & \cdots & C_{1r} \\ C_{21} & C_{22} & \cdots & C_{2r} \\ \vdots & \vdots & \ddots & \vdots \\ C_{s1} & C_{s2} & \cdots & C_{sr} \end{bmatrix} = \begin{bmatrix} C_1 \\ C_2 \\ \vdots \\ C_s \end{bmatrix}, \qquad [5.3]$$

Where $C_{ii}$ is the SISO-PID controller relative to monitor j and drug i; $C_1$ is the MISO-PID-ePPF control subsystem; $C_2$ is the MISO-PID-eRMF control subsystem; and $C_3$ is the MISO-PID-eNMB control subsystem. The $C_{ij}$ are defined by the proportional gains matrix $[K_P]$; the integral gains matrix $[K_I]$ and the derivative earnings matrix $[K_D]$:

$$[K_P] = \begin{bmatrix} K_{P11} & K_{P12} & \cdots & K_{P1r} \\ K_{P21} & K_{P22} & \cdots & K_{P2r} \\ \vdots & \vdots & \ddots & \vdots \\ K_{Ps1} & K_{Ps2} & \cdots & K_{Psr} \end{bmatrix} = \begin{bmatrix} K_{P1} \\ K_{P2} \\ \vdots \\ K_{Ps} \end{bmatrix}, \qquad [5.4]$$

$$[K_I] = \begin{bmatrix} K_{I11} & K_{I12} & \cdots & K_{I1r} \\ K_{I21} & K_{I22} & \cdots & K_{I2r} \\ \vdots & \vdots & \ddots & \vdots \\ K_{Is1} & K_{Is2} & \cdots & K_{Isr} \end{bmatrix} = \begin{bmatrix} K_{I1} \\ K_{I2} \\ \vdots \\ K_{Is} \end{bmatrix}, \qquad [5.5]$$

$$[K_D] = \begin{bmatrix} K_{D11} & K_{D12} & \cdots & K_{D1r} \\ K_{D21} & K_{D22} & \cdots & K_{D2r} \\ \vdots & \vdots & \ddots & \vdots \\ K_{Ds1} & K_{Ds2} & \cdots & K_{Dsr} \end{bmatrix} = \begin{bmatrix} K_{D1} \\ K_{D2} \\ \vdots \\ K_{Ds} \end{bmatrix}, \qquad [5.6]$$

$$K_p = diag([K_P]) \qquad [5.7]$$

$$K_I = diag([K_I]) \qquad [5.8]$$

$$K_D = diag([K_D]) \qquad [5.9]$$

Where $K_{Pij}$ is the proportional gain relative to monitor j and drug l; $K_{Iij}$ is the integral gain relative to monitor j and drug l; and Kai is the derivative gain relative to monitor j and drug l; $K_{Pi}$ is the vector of proportional gains relative to drug l; $K_{Ii}$ is the vector of integral gains relative to drug l; $K_{Di}$ is the vector of derivative gains relative to drug l; $K_P$ is the vector of direct proportional gains relative to drug j and to the monitor y; $K_I$ is the vector of direct integral gains relative to drug j and to monitor y; and $K_D$ is the vector of direct derivative gains relative to drug j and monitor j.

5.2.2.—[SYN] is the drug synergy matrix:

$$[SYN] = \begin{bmatrix} S_{11} & S_{12} & \cdots & S_{1r} \\ S_{21} & S_{22} & \cdots & S_{2r} \\ \vdots & \vdots & \ddots & \vdots \\ S_{s1} & S_{s2} & \cdots & S_{sr} \end{bmatrix}^T = \begin{bmatrix} S_1 \\ S_2 \\ \vdots \\ S_s \end{bmatrix}^T, \qquad [5.10]$$

Where $S_{ij}$ is the synergy relative to the controller $C_{ij}$, $S_i$ is the synergy vector relative to the drug i.

5.2.3.—$K_{ol}$ is a vector of gains on the manual protocol infusion vector (4), $$K_{ol} = [K_{ol1} K_{ol2} \ldots K_{ols}]^T, \qquad [5.11]$$

Where $K_{ol1}$ is the gain that modulates the infusion of the manual protocol of the ePPF (4.1); $K_{ol2}$ is the gain that modulates the infusion of the manual protocol of the eRMF (4.2); $K_{ol3}$ is the gain that modulates the infusion of the manual protocol of the eRCN (4.3) and $K_{ol4}$ to $K_{ols}$ are the gains that modulate the infusions of the manual protocol of the new drugs that can be incorporated in the control system;

$$K_{ol} = \begin{cases} 1, & y_T \le y_f, \\ \dfrac{y_f}{y_T - y_{LO}} - \dfrac{y_{LO}}{y_T - y_{LO}}, & y_{LO} \le y_f \le y_T, \\ 0, & \text{otherwise}, \end{cases} \quad [5.12]$$

Where $y_\tau$ is the target vector of the monitored variables (8); $y_f$ is the filtered monitoring variables vector (10) and $y_{Lo}$ is the vector of lower thresholds of activation of the correction.

5.3.—Defining the MISO-PID control subsystems (25, 26, 27) from the control error vectors (12, 13, 14) and the manual protocol infusion vector (4), $$u_1 = C_{11} \cdot S_{11} + C_{12} \cdot S_{12} + \ldots + C_{1r} \cdot S_{1r} + K_{ol1} \cdot u_{ol1} \quad [5.13]$$

$$u_2 = C_{21} \cdot S_{21} + C_{22} \cdot S_{22} + \ldots + C_{2r} \cdot S_{2r} + K_{ol2} \cdot u_{ol2},$$

$$\ldots$$

$$u_s = C_{s1} \cdot S_{s1} + C_{s2} \cdot S_{s2} + \ldots + C_{sr} \cdot S_{sr} + K_{ols} \cdot u_{ols}$$

Where $C_{ij}$ is the PID controller relative to monitor j and drug i; $S_{ij}$ is the synergy relative to controller $C_{ij}$; and $K_{oli}$ is the gain applied to the infusions of the manual protocol of the drug $u_{oli}$.

5.3.1.—Defining each SISO-PID controller (25.1, 27.3) by means of the control error vectors (12, 13, 14) and the gains defined in step 5.2.1, $$C_{ij} = P_{ij} + I_{ij} + D_{ij}, \quad [5.14]$$

Where i Identifies the drug (15.1) and j Identifies the monitor (10.j); $P_{ij}$ is the proportional action, $I_{ij}$ is the integral action and $D_{ij}$ is the derivative action.

5.3.2.—Calculating the proportional, integral and derivative action;

$$P_{ij} = K_{Pij} \cdot e_{Pj} \quad [5.15]$$

$$I_{ij} = K_{Iij} \int e_{Ij} d\tau, \quad$$

$$D_{ij} = K_{Dij} \dfrac{de_{Fj}}{dt}$$

Where $K_{Pij}$ is the proportional gain associated with drug i and monitor j; $e_{pj}$ is the proportional error related to monitor j; $K_{Iji}$ is the integral gain associated with drug i and the monitor; $e_{Ii}$ is the integral error related to drug i and the monitor; $K_{Dij}$ is the derivative gain associated with drug i and the monitor; and $e_{Fj}$ is the filtered derivative error related to drug j.

Step 6) executed by the SynPID control system further comprises an infusion correcting system (17) for:

6.1.—Defining the correction vector (18), $$u_{cr} = [u_{cr1} u_{cr2} \ldots u_{crs}]^T \quad [6.1]$$

Where $u_{cr1}$ is the corrective infusion of the ePPF drug (18.1); $u_{cr2}$ is the corrective infusion of the eRMF drug (18.2); $u_{cr3}$ is the corrective infusion of the eRCN drug (18.3); and the other components of the vector from $u_{cr4}$ to $u_{crs}$ are other possible corrections of other drugs incorporated into the system.

6.2.—Calculating the correction vector (18) from the filtered monitoring variables vector (10), $$u_{cr} = \begin{cases} K_P^T \cdot [SYN] \cdot [-y_{HI} + y_f], & y_{HI} \le y_f, \\ K_P^T \cdot [SYN] \cdot [-y_{LO} + y_f], & y_{LO} \ge y_f, \\ 0, & \text{otherwise} \end{cases} \quad [6.2]$$

Where $[K_P]$ is the proportional gain matrix, equation [5.4]; [SYN] is the synergy matrix, equation [5.10]; and f is the filtered monitoring variables vector (10).

6.2.1.—$y_{HI}$ is the vector of upper thresholds of activation of the correction, $$y_{HI} = [H_1 H_2 \ldots H_r]^T \quad [6.3]$$

Where $H_1$ is the upper threshold relative to the eBIS monitor; $H_2$ is the upper threshold relative to the eNOX monitor; $H_3$ is the upper threshold relative to the eNMB monitor; and the other components of the vectors from $H_4$ to $H_r$ are the upper thresholds of other possible monitor additions to the system.

6.2.2.—$y_{LO}$ is the vector of the lower thresholds of activation of the correction, $$y_{LO} = [L_1 L_2 \ldots L_r]^T \quad [6.4]$$

Where $L_1$ is the lower threshold relative to the eBIS monitor; $L_2$ is the lower threshold relative to the eNOX monitor; $L_3$ is the lower threshold relative to the eNMB monitor; and the other components of the vectors from $L_4$ to $L_r$ are the lower thresholds of other possible monitor additions to the system.

Step 7) of the SynPID control system further comprises a security system (19) for:

7.1.—Defining the reliable control vector (20), $$u_{sf} = [u_{sf1} u_{sf2} \ldots u_{sfs}]^T \quad [7.1]$$

Where usf1 is the reliable infusion of the ePPF drug (20.1); Usf2 is the reliable infusion of the eRMF drug (20.1); Usf3 is the reliable infusion of the eRCN drug (20.1); and the remaining components of the vector from usf4 to usfs are other possible reliable infusions of other drugs incorporated to the system.

7.2.—Calculating the reliable control vector (20) from the control infusion vector (15) and the correction vector (18), $$u_{sf} = \begin{cases} u_{HI}, & u_{pid} + u_{cr} \ge u_{HI} \\ u_{pid} + u_{cr}, & u_{LO} < u_{pid} + u_{cr} \le u_{HI}, \\ u_{LO}, & u_{pid} + u_{cr} \le u_{LO} \end{cases} \quad [1] \; [7.2]$$

Where $u_{cr}$ is the correction vector (18) and $u_{pid}$ is the control infusion vector (15).

7.2.1.—$U_{HI}$ is the drug infusion upper limit vector, $$u_{HI} = [u_{H1} u_{H2} \ldots u_{Hs}]^T, \quad a) \; [7.3]$$

Where $u_{H1}$ is the upper limit of the infusion relative to the ePPF drug; $u_{H2}$ is the upper limit of the infusion relative to the eRMF drug; $u_{H3}$ is the upper limit of the infusion relative to the eRCN drug; and the other components of the vectors from $u_{H4}$ to $u_{Hs}$ are the upper limits of the infusions relative to other possible drug incorporations into the system.

7.2.2.—$u_{LO}$ is the lower bound vector for drug infusion, $$u_{LO}=[u_{L1}u_{L2}\ldots u_{Ls}]^T, \qquad [1][7.4]$$

Where $u_{L1}$ is the lower limit of the infusion relative to the ePPF drug; $u_{L2}$ is the lower limit of the infusion relative to the eRMF drug; $u_{L3}$ is the lower limit of the infusion relative to the eRCN drug; and the other components of the vectors from $u_{L4}$ to $u_{Ls}$ are the lower limits of the infusions relative to other possible drug incorporations into the system.

Step 8) executed by the SynPID control system further comprises a quantification system (21) for:

8.1.—Defining the vector of automatic infusions (22), $$u_{cI}[u_{cI1}u_{cI2}\ldots u_{cIs}]^T, \qquad [8.1]$$

Where $u_{cI1}$ is the automatic infusion of the ePPF drug (22.1); $u_{cI2}$ is the automatic infusion of the eRMF drug (22.2); u cl3 is the automatic infusion of the eRCN drug (22.3); and the other components of the vector from $u_{cI4}$ to $u_{cI5}$ are other possible automatic infusions in CL of other drugs incorporated into the system.

8.2.—computing the automatic infusion vector (22) from the reliable control vector (20), $$u_{cI} = \text{round}\left(\frac{u_{sf}}{u_{mn}}\right)\cdot u_{mn}, \qquad [8.2]$$

Where $u_{sf}$ is the reliable control vector (20) and $u_{mn}$ is the resolution vector of the continuous infusion pump system (2);

8.2.1.—$u_{min}$ is the resolution vector of each drug infusion pump;

$$u_{mn}[u_{mn1}u_{mn2}u_{mns}]^T, \qquad [8.3]$$

Where $u_{mn}1$ is the resolution of the ePPF drug infusion pump; $u_{mn2}$ is the resolution of the eRMF drug infusion pump; $u_{mn3}$ is the resolution of the eRCN drug infusion pump; and the other vector components from u mn4 to $u_{mns}$ are the resolutions of other possible new drug infusion pumps incorporated into the control system.

Step 9) executed by the SynPID control system further comprises a switching system (23) for:

9.1.—Defining the anesthetic drug infusion vector (5), $$u_{pt}=[u_{pt1}u_{pt2}\ldots u_{pts}]^T, \qquad [9.1]$$

Where $u_{pt1}$ is the infusion of the ePPF drug (5.1); $u_{pt2}$ is the continuous infusion of the eRMF drug (5.2); $u^{pt3}$ is the infusion of the eRCN drug (5.3); and the other components of the vector from $u_{pt4}$ to $u_{pts}$ are other possible infusions of new drugs incorporated into the control system.

9.2.—Calculating the anesthetic drug infusion vector (5) from the manual protocol infusion vector (4) and the automatic infusion vector (22), $$u_{pt} = \begin{cases} u_{oI}, & t_i \leq t < t_m, \\ u_{cI}, & t_m \leq t < t_r, \\ 0, & t_r \leq t, \end{cases} \qquad [9.2]$$

Where $u_{oI}$ is the manual protocol infusion vector (4); $u_{cI}$ is the automatic infusion vector (22); $t_i$ is the start time of the IPh; $t_m$ is the start time of the MPh; and $t_r$ is the start time of the RPh.

Step 10) executed by the SynPID control system further comprises of a MISO-PID-ePPF control subsystem (25) for:

10.1.—Defining the MISO-PID-ePPF control subsystem (25) as a set of SISO-PID controllers, $$C_1=[C_{11}C_{12}\ldots C_{1r}]^T, \qquad [10.1]$$

10.2.—Calculating the control infusion of the ePPF (15.1); from the SISO-PID controllers (25.1, 25.2, 25.3), the control error vectors (12, 13, 14) and the infusion of ePPF of the manual protocol (4.1), $$u_1=C_1\cdot S_1+K_{oI1}\cdot u_{oI1}$$

$$u_1=C_{11}\cdot S_{11}+C_{12}\cdot S_{12}+\ldots+C_{1r}\cdot S_{1r}+K_{oI1}\cdot u_{oI1}, \qquad [10.2]$$

Where $S_i$ is a vector formed by the first row of [SYN]; $C_{1j}$ is the PID controller relative to the monitor j and the ePPF drug; $S_{1j}$ is a vector formed by the synergy relative to the controller $C_{1j}$ and $K_{oI1}$ is the gain applied to the manual protocol infusion of the ePPF.

Step 11) executed by the SynPID control system further comprises of a MISO-PID-eRMF control subsystem (26) for:

11.1.—Defining the MISO-PID-eRMF control subsystem (26) as a set of SISO-PID controllers, $$C_2=[C_{21}\ C_{22}\ldots C_{2r}]^T, \qquad [11.1]$$

11.2.—Calculating the control infusion of the eRMF (15.2); from the SISO-PID controllers (26.1, 26.2, 26.3), the control error vectors (12, 13, 14) and the manual protocol infusion of eRMF (4.2), $$u_2 C_2\cdot S_2+K_{oI2}\cdot u_{oI2}$$

$$u_2=C_{21}\cdot S_{21}+C_{22}\cdot S_{22}+\ldots+C_{2r}\cdot S_{2r}+K_{oI2}\cdot u_{oI2}, \qquad [11.2]$$

Where $S_2$ is a vector formed by the second row of [SYN]; $C_{2j}$ is the PID controller relative to the monitor j and the eRMF drug; $S_{2j}$ is a vector formed by the synergy relative to the controller $C_{2j}$ and $K_{oI2}$ is the gain applied to the infusion of the manual protocol of the eRMF.

Step 12) executed by the SynPID control system further comprises of a MISO-PID-eNMB control subsystem (27) for:

10.1.—Defining the MISO-PID-eNMB control subsystem (27) as a set of SISO-PID controllers, $$C_3+[C_{31}C_{32}\ldots C_{3r}]^T, \qquad [12.1]$$

12.2.—Calculating the control infusion of the eRCN (15.3); from the SISO-PID controllers (27.1, 27.2, 27.3), the control error vectors (12, 13, 14) and the manual protocol infusion of eRCN (4.3), $$u_3=C_3\cdot S_3+K_{oI3}\cdot u_{oI3}$$

$$u_3=C_{31}\cdot S_{31}+C_{32}\cdot S_{32}+\ldots+C_{3r}\cdot S_{3r}+K_{oI3}\cdot u_{oI3}, \qquad [12.2]$$

Where $S_3$ is a vector formed by the third row of [SYN]; $C_{3j}$ is the PID controller relative to the monitor j and the eRCN drug; $S_{3j}$ is the synergy relative to the controller $C_{3j}$ and $K_{ol3}$ is the gain applied to the of manual protocol infusion of eRCN.

Step 13) executed by the SynPlD control system may further comprise several MISO-PID controllers for new drugs:

13.1, —Defining the MISO-PID controller for drug i as a set of SISO-PID controllers, $$C_i=[C_{i1}C_{i2}\ldots C_{ir}]^T, \qquad [13.1]$$

Where identifies the new drugs; and r identifies the number of monitors.

13.2. —Calculating the control infusion of drug i; from the SISO-PID controllers, the control errors and the manual protocol infusion of drug i (4.i), $$u_i=C_i \cdot S_i+k_{oli} \cdot o_{oli} \qquad [13.2]$$

Another aspect of the invention discloses an anesthetic drug multi-infusion device with synergy by control in CL MIMO-PID (SynPlD) applied in IV anesthetic acts; this method is multidimensional and configurable to the number of drugs used and the number of monitoring variables that are used, in any of the embodiments of the first aspect of the invention.

The anesthetic drug multi-infusion device with synergy by control in CL MIMO-PID (SynPlD) applied in IV anesthetic acts comprises at least one filter bank (9); a control error generator (11); a multivariable and synergistic controller MIMO-PID (16); an infusion correction system (17); a safety system (19); a quantification system (21); and a switching system (23). The multi-infusion device of anesthetic drugs with synergy by control in CL MIMO-PID (SynPlD) applied in anesthetic acts by IV can be an electronic or electromechanical device.

DETAILED DESCRIPTION OF THE INVENTION

Figure 1:
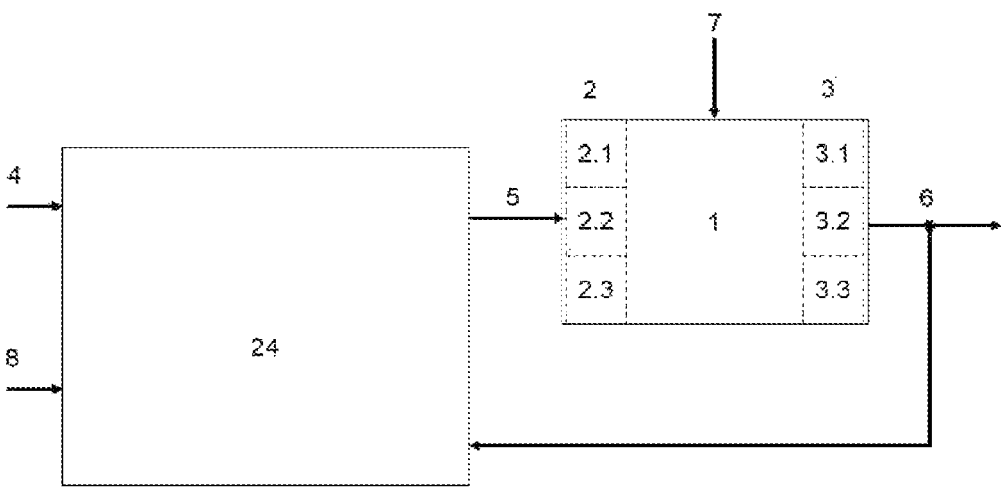
FIG. 1 shows the topology of the SynPlD control system (24) in its most general form, showing the patient (1) to which the anesthetic drug infusion vector (5) is supplied through an infusion pump system (2) and from which the measurements of the monitoring variables vector (6) are gathered by the monitoring equipment (3). The infusion pumps control the drugs ePPF (2.1), eRMF (2.2) and eRCN (2.3). The monitoring equipment (3) collects information on the following variables: 1) DoH (3.1) via the eBIS monitor (6.1); 2) ANG (3.2) via the eNOX monitor (6.2); and 3) MRX (3.3) via the eNMB monitor (6.3). The monitoring variables vector (6) is the feedback base of the SynPlD control system (24), which also uses information on: 1) the monitored variables target vector (8): eBIS (8.1), eNOX target (8.2) and eNMB target (8.3); and 2) the manual protocol infusion vector (4): ePPF manual protocol (4.1), eRMF manual protocol (4.2) and eRCN manual protocol (4.3).
Figure 2:
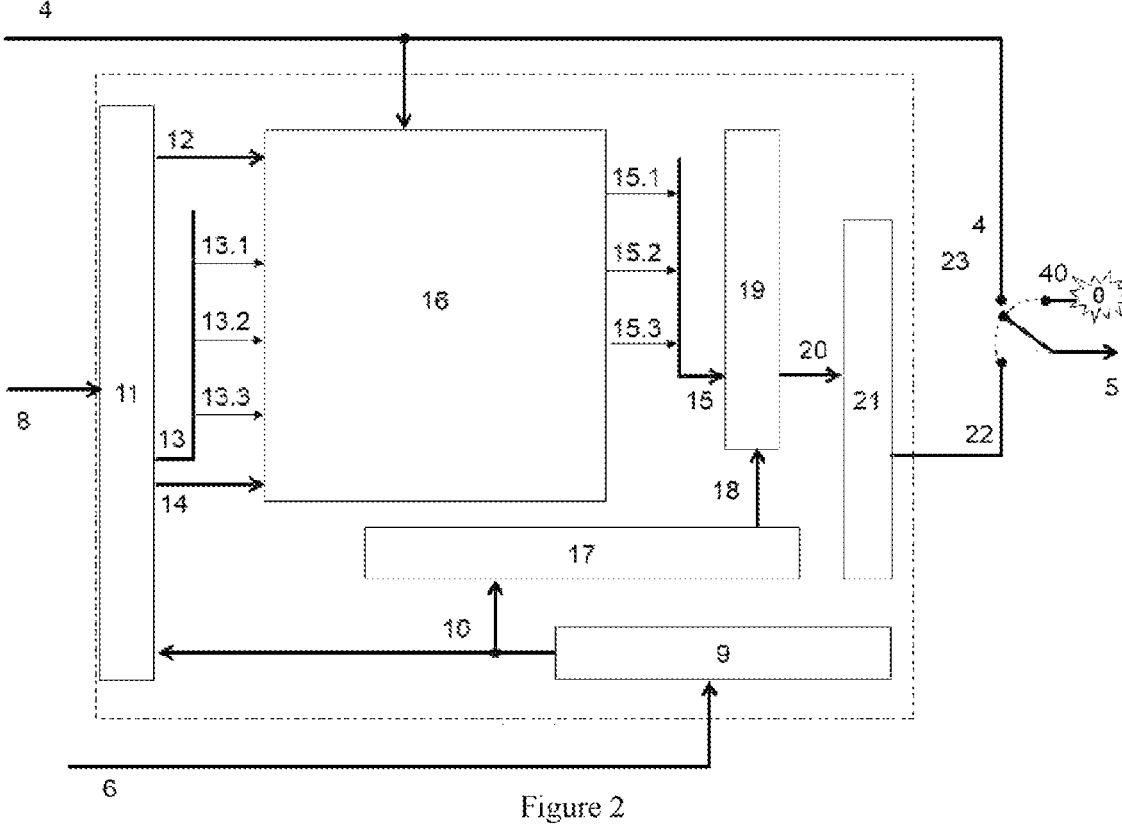
FIG. 2 shows a detailed view of the SynPlD control system (24) that has as inputs: 1) the manual protocol infusion vector (4); 2) the monitored variables target vector (8); and 3) the values of the monitoring variables vector (6). The SynPlD control system (24) is composed of: 1) a filter bank (9) for obtaining a filtered monitoring variables vector (10) from the monitoring variables vector (6); the filter bank (9) is composed of three filters, one for cleaning and filtering the eBIS (9.1), another for cleaning and filtering the eNOX (9.2) and another for cleaning and filtering the eNMB (9.3); 2) a control error generator (11) for obtaining the control error vectors (12, 13, 14) from the filtered monitoring variable vector (10) and the target monitored variables vector (8); specifically, this consists of obtaining the eBIS monitor control error vector (12); obtaining the eNOX monitor control error vector (13) and obtaining the eNMB monitor control error vector (14); 3) a multivariable and synergistic MIMO-PID controller (16) to obtain a control infusion vector (15) from the control error vectors (12, 13, 14) and from the manual protocol infusion vector (4); 4) an infusion correcting system (17) for obtaining a correction vector (18) from the filtered monitored variables vector (10); 5) a safety system (19) for obtaining a reliable control vector (20) from the control infusion vector (15) and the correction vector (18); 6) a quantifier (21) for obtaining an automatic infusion vector (22) from the reliable control vector (20); and 7) a switching system (23) for obtaining the anesthetic drug infusion vector (5) from the manual protocol infusion vector (4) and the automatic infusion vector (22).
Figures 3, 4:
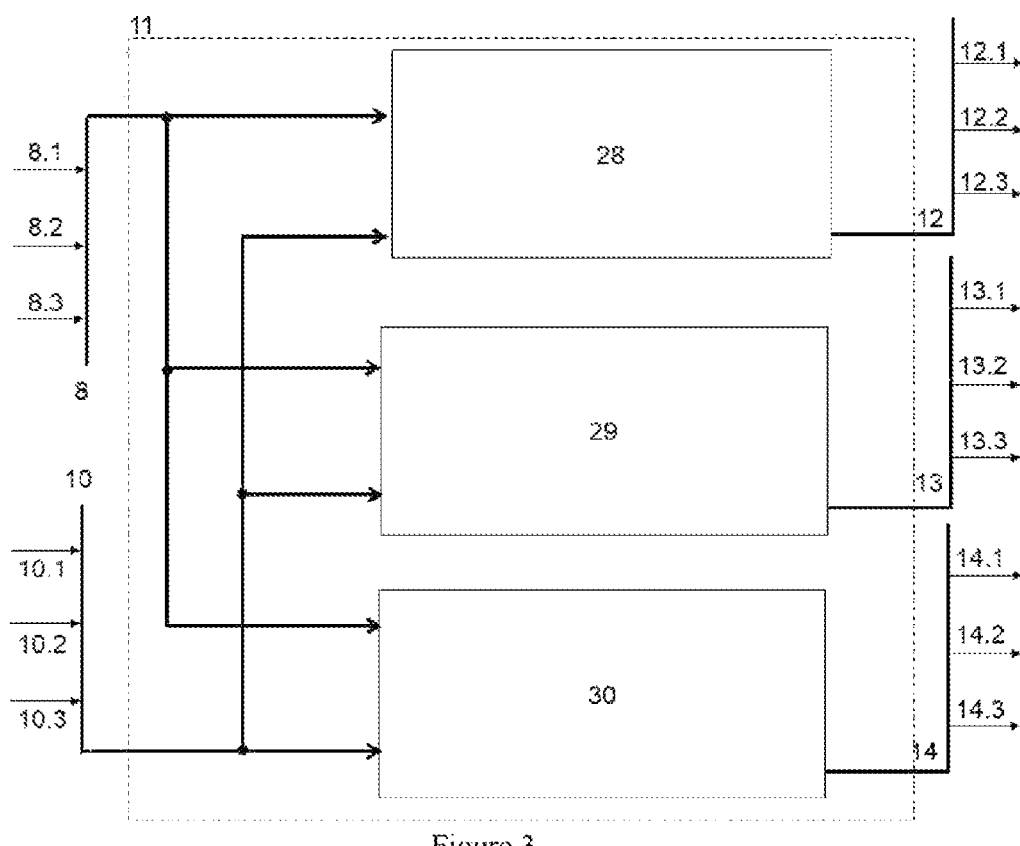
FIG. 3 shows a detailed view of the control error generator (11) which has as inputs: 1) the monitored variables target vector (8); and 2) the filtered monitoring variables vector (10). The control error generator (11) is composed of: 1) a DoH error generator (28) from where the eBIS monitor control error vector (12) is obtained, where the proportional error eBIS (12.1), the integral error eBIS (12.2) and the derivative error eBIS (12.3) are indicated, based on the filtered monitoring of the DoH by the eBIS monitor (10.1) and its target value (8.1); 2) an ANG error generator (29) where the eNOX monitor control error vector (13) is obtained, wherein the eNOX proportional error (13.1), the eNOX integral error (13.2) and the eNOX derivative error (13.3) are indicated, from the filtered monitoring of the ANG by the eNOX monitor (10.2) and its target value (8.2); and 3) an MRX error generator (30) where the eNMB monitor control error vector (14) is obtained, wherein the eNMB proportional error (14.1), the eNMB integral error (14.2) and the eNMB derivative error (14.3) are indicated, based on the filtered monitoring of the MRX using the eNMB monitor (10.3) and its target value (8.3).
FIG. 4 shows a detailed view of the multivariable controller with MIMO-PID synergy (16) that has as inputs the control error vectors (12, 13, 14) and the manual protocol infusion vector (4). The MIMO-PID multivariable and synergistic controller (16) is composed of miscellaneous MISO-PID control subsystems (25, 26, 27) that relate the control error vectors (12, 13, 14) to the control infusion vector (15).

The present invention provides to the art various strategies of complementing the PID controller in CL to be effective in the control in CL of the Induction and maintenance of the general anesthesia, calculating the dose of the ePPF, eRMF and eRCN drugs based on a control error vector. Control in CL is obtained in a novel way by considering the synergy of the drugs in the act of anesthesia and by the feedback of the monitoring information of DoH, ANG and MRX (other variables can be considered) through the eBIS, eNOX and eNMB monitors respectively (other monitors can be considered). The changes in the values of the monitors are mainly caused by the effect of drugs and the acts of surgery.

In addition, drug infusions are conditioned by a safety system to safeguard the physical integrity of the patient and are complemented by an infusion correction system that the classic PID does not have. Among its novelties, it presents the consideration of the synergy between drugs in a PID multi-controller, asymmetry in control errors, correction of infusion for exceptionally low or high levels in monitors, safety against overinfusion through fixed or variable limits of drug infusion and by suspension of pumps, safety against underinfusion due to conditions related to the manual experience of the anesthesiologist (OL manual protocol). Finally, the final decision on the infusions is conditioned with a quantifier to adapt the infusions to the resolutions of the electromechanical infusion pumps.

The final objective is to perform an automatic calculation of the infusions of ePPF, eRMF and eRCN that would be applied directly to a patient under surgery under general anesthesia, who would be the end user of the present invention. The proposed invention has among its novelties the definition of a new anesthetic drug infusion system with a SynPlD control system, formed by a filter bank, an asymmetric control error generator, a MIMO-PID controller, a correction system, a safety system and a quantification system that can be applied to the patient under surgery, since it takes into account: 1) monitoring of the DoH, ANG and MRX using eBIS, eNOX and eNMB monitors; 2) the infusion pumps of the ePPF, eRMF and eRCN drugs; and 3) the use of an electronic device that uses a microprocessor and a storage memory.

In addition, to estimate the automatic infusions on the patient, the CL control system considers the previous drug infusions at the time of action and considers the measurements of current and past monitors.

The continuous infusion system of ePPF, eRMF and eRCN drugs with SynPlD control system is a control method that requires the manual experience of the anesthesiologist (OL manual protocol) and is customized for each patient using a variant of the Cohen-Coon empirical adjustment method using the proportional, integral and derivative gains of each SISO-PID controller, the patient's weight (W), height (H), sex (G) and muscle mass (MB). The customization method is applied during the IPh of general anesthesia.

The SynPlD control system (24) proposes the anesthetic drug infusion vector (5), as a result of the application of the switching system (23), which initially applies the manual protocol infusion vector (4) in the IPh, to switch the automatic infusion vector (22) in MPh and override the infusion in RPh.

The main objective of the SynPlD control system (24) is to take the patient (1) to a satisfactory and reliable anesthesia state based on: 1) the current anesthesia state; 2) the vector of current and/or past monitoring variables (6) (history stored in memory); and 3) the vector of infusion of anesthetic drugs (5) of past times (history stored in memory). The invention consists in the proposal of an electronic system in which a feedback control algorithm is executed defined by a SynPlD control system (24) based on a multivariable controller and with MIMO-PID synergy (16) that defines the multivariable control system to perform the control of a reliable anesthetic state in patients (1) undergoing surgery under general anesthesia.

The SynPlD control system is implemented in a microprocessor-based system with memory selected from: smartphones, tablets, personal computers, arduino, raspberry-PI and specific hardware for the execution of the method or use the hardware of the infusion pumps to execute the sequence of instructions that would implement the drug infusion method in a SynPlD control system described in the present invention.

The synergistic drug infusion system by control in CL MIMO-PID (SynPlD) applied in IV anesthetic acts of the present invention differs from the prior art methods based on classical PIDs in at least the following aspects:

The SynPlD control system uses three control phases controlled by the switching system (23): 1) IPh, the phase corresponding to the beginning of the anesthetic act and lasts until a satisfactory anesthetic state is achieved; during this period only the manual protocol infusion vector (4) is applied to the patient (1), while the end of this period is used for the customization of the SynPlD control system (24) to the patient (1); 2) MPh, in this phase it is where the surgery takes place and the objective of the SynPlD control system is to maintain the satisfactory anesthetic state, despite the surgical acts; and 3) RPh, in this phase the infusions of the drugs are removed to achieve patient awareness.

The SynPlD control system uses a filter bank (9) to remove noise and artifacts from the monitoring variable vector (6) and obtain the filtered monitoring vector. The filter bank (9) is based on spectral cleaning and decision-making based on monitoring conditions.

The SynPID control system uses a control error generator (11) relating to the eBIS, eNOX and eNMB monitors that make up the monitoring variable vector (6); the errors are asymmetric and are defined by a modulation of the target vector of the monitored variables (8) and the filtered monitoring variable vector (10). The vector of surgical actions (7) is reflected in the patient (1) through variations in the monitoring variables vector (6).

The SynPID control system uses a control infusion vector (15) formed by infusions of the drugs ePPF (15.1), eRMF (15.2) and eRCN (15.3). Each drug infusion is defined by the action of a MISO-PID control system composed of the sum of three control actions relating to three SISO-PID controllers.

Figure 5:
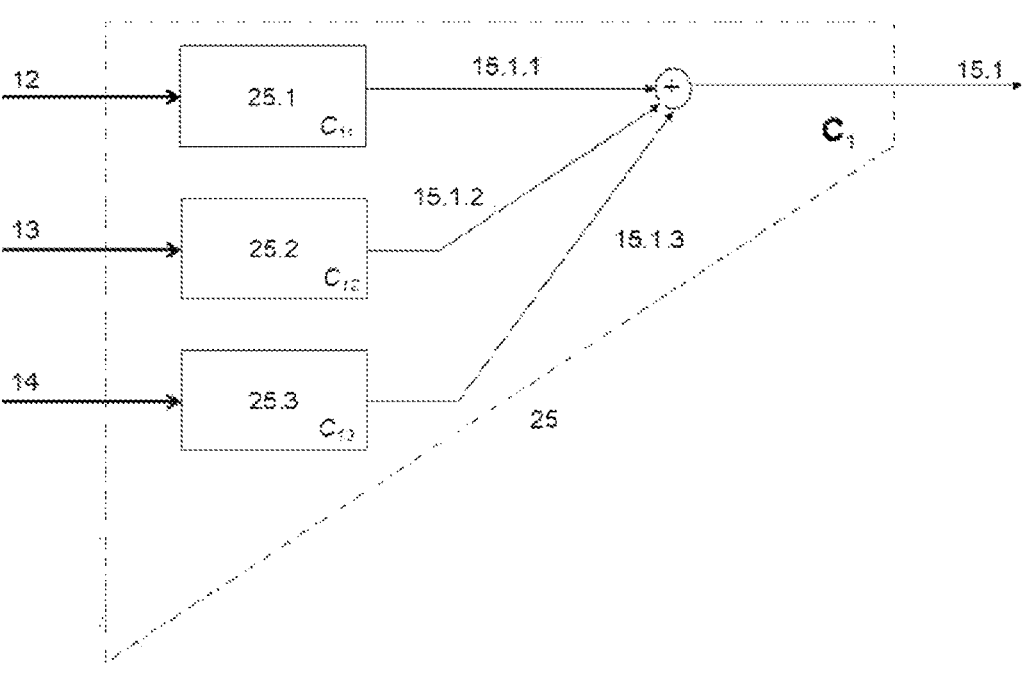
FIG. 5 shows a detailed view of the MISO-PID controller (25) related to the infusion of the ePPF drug (15.1) that has as inputs the control error vectors (12, 13, 14). The MISO-PID-ePPF control subsystem (25) is composed of three SISO-PID controllers that relate the infusion of the ePPF drug with: 1) the eBIS control error vector (12) via an eBIS-ePPF PID controller (25.1); 2) the eNOX control error vector (13) via an eNOX-ePPF PID controller (25.2); and 3) the eNMB control error vector (14) via an eNMB-ePPF PID controller (25.3).
Figure 6:
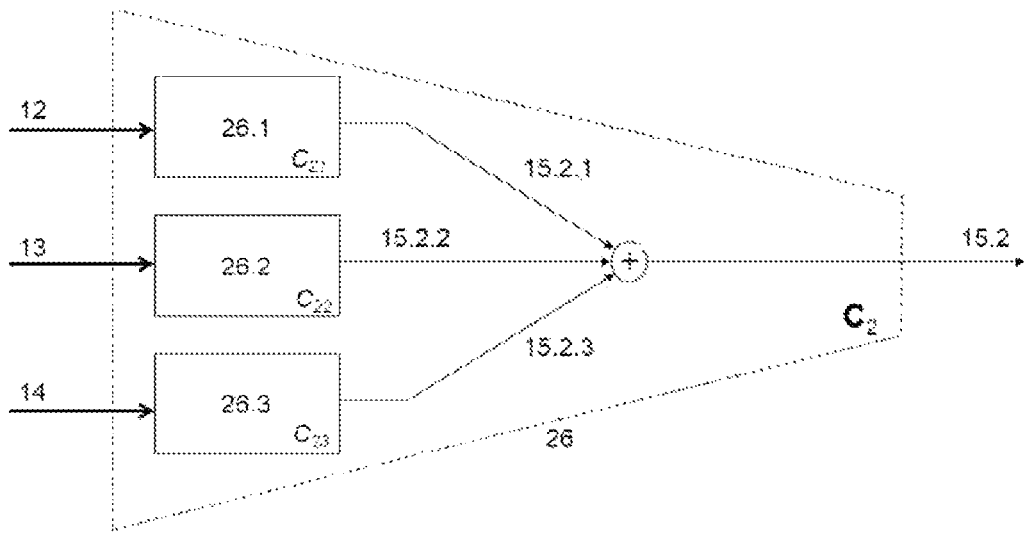
FIG. 6 shows a detailed view of the MISO-PID-eRMF control subsystem (26) related to the infusion of the eRMF drug (15.2) that has as inputs the control error vectors (12, 13, 14). The MISO-PID-eRMF control subsystem (26) is composed of three SISO-PID controllers that relate the infusion of the eRMF drug with: 1) the eBIS control error vector (12) via an eBIS-eRMF PID controller (26.1); 2) the eNOX control error vector (13) via an eNOX-eRMF PID controller (26.2); and 3) the eNMB control error vector (14) via an eNMB-ePPF PID controller (26.3).
Figure 7:
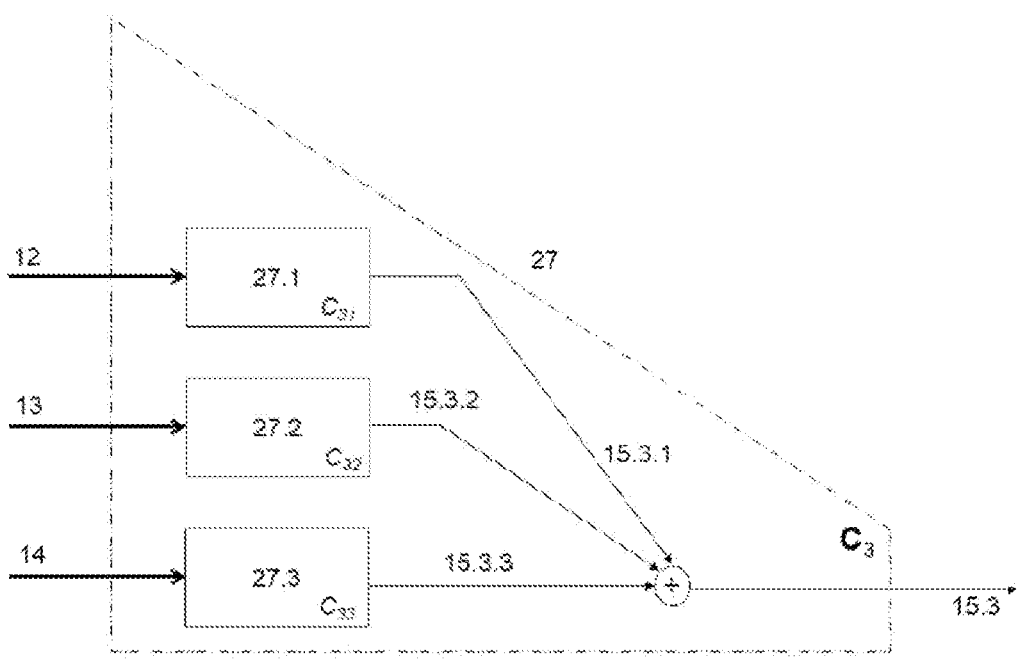
FIG. 7 shows a detailed view of the MISO-PID-eNMB control subsystem (27) related to the infusion of the eRCN drug (15.3) that has as inputs the control error vectors (12, 13, 14). The MISO-PID-eNMB control subsystem (27) is composed of three SISO-PID controllers that relate the infusion of the eRCN drug with: 1) the eBIS control error vector (12) via an eBIS-eRCN PID controller (27.1); 2) the eNOX control error vector (13) via an eNOX-eRCN PID controller (27.2); and 3) the eNMB control error vector (14) via an eNMB-eRCN PID controller (27.3).
Figure 8:
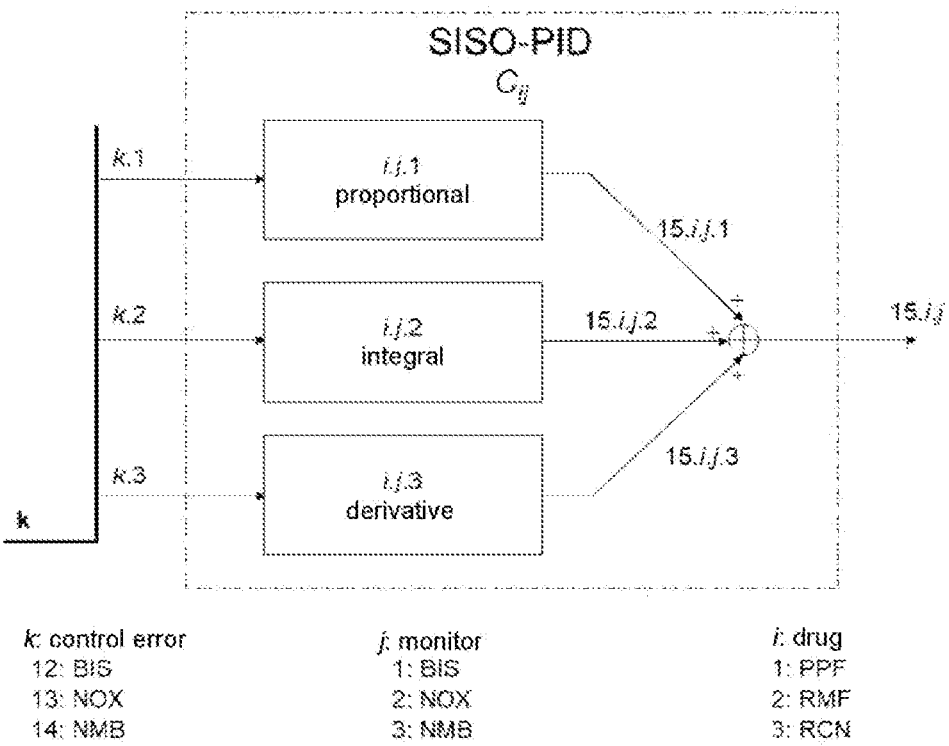
FIG. 8 shows a detailed view of one of the 9 SISO-PID controllers (Cu) that make up the SynPlD control system (24); each SISO-PID controller has as inputs the corresponding proportional (k.1), integral (k.2) and derivative (k.3) errors, relative to each component of each control error vector ($e_j$). Each SISO-PID controller is identified with the subscripts/that identifies the drug to which the partial infusion is being calculated, and j that identifies the origin of the monitor. Thus i=1 Identifies the PPF, i=2 the RMF and i=3 the RCN, j=1 Identifies the monitor BIS, j=2 the NOX and j=3 the NMB, k=12 Identifies the error vector relative to the monitor BIS, k=13 the one relative to the NOX and k=14 the NMB.

The infusion of ePPF (15.1) is calculated by the sum of:
1) a SISO-PID controller (25.1) that relates a portion of the ePPF control infusion to the eBIS monitor control error vector (12), formed by a proportional component (12.1), an integral component (12.2), and a derivative component (12.3); 2) a SISO-PID controller (25.2) that relates a portion of the ePPF control infusion to the eNOX monitor control error vector (13), formed by a proportional component (13.1), an integral component (13.2), and a derivative component (13.3); and 3) a SISO-PID controller (25.3) that relates a portion of the ePPF control infusion to the eNMB monitor control error vector (14), formed by a proportional component (14.1), an integral component (14.2), and a derivative component (14.3);

The infusion of eRMF (15.2) is calculated by the sum of: 1) a SISO-PID controller (26.1) that relates a portion of the control infusion of the eRMF to the control error vector of the eBIS monitor (12), formed by a proportional component (12.1), an integral component (12.2) and a derivative component (12.3); 2) a SISO-PID controller (26.2) that relates a portion of the control infusion of the eRMF to the control error vector of the eNOX monitor (13), formed by a proportional component (13.1), an integral component (13.2) and a derivative component (13.3); and 3) a SISO-PID controller (26.3) that relates a portion of the control infusion of the eRMF to the control error vector of the eNMB monitor (14), formed by a proportional component (14.1), an integral component (14.2) and a derivative component (14.3);

The infusion of eRCN (15.3) is calculated by the sum of: 1) a SISO-PID controller (27.1) that relates a portion of the eRCN control infusion to the eBIS monitor control error vector (12), formed by a proportional component (12.1), an integral component (12.2), and a derivative component (12.3); 2) a SISO-PID controller (27.2) that relates a portion of the eRCN control infusion to the eNOX monitor control error vector (13), formed by a proportional component (13.1), an integral component (13.2), and a derivative component (13.3); and 3) a SISO-PID controller (27.3) that relates a portion of the eRCN control infusion to the eNMB monitor control error vector (14), formed by a proportional component (14.1), an integral component (14.2), and a derivative component (14.3);

The SynPID control system (24) uses 9 SISO-PID controllers, grouped into three MISO-PID control subsystems (FIGS. 5, 6 and 7), each SISO-PID controller (C) (FIG. 8) being used to calculate drug infusion i (15.i):

A proportional action system (i.j.1) that defines at its output the proportional infusion action (15.i.1), starting from its input which is the proportional asymmetric control error (k.1).

An integral action system (i.j.2) that defines at its output the integral infusion action (15.i.2), starting from its input which is the integral symmetric control error of (k.2).

A derivative action system (i.j.3) that defines at its output the derivative infusion action (15.i.3), from its input which is the asymmetric derivative control error (k.3).

The SynPID control system (24) uses an infusion correction system (17), which compensates the control infusion vector (15) with the correction vector (18) which are defined by the deviations of the vector of filtered monitoring variables (10) with respect to some vectors of upper and lower thresholds. These deviations could not be corrected by the multivariable control based on PIDs (24).

The SynPID control system (24) uses a safety system (19), which conditions the control infusion vector (15) compensated by the correction vector (18) to lead to the reliable control vector (20), which prevents overinfusion and underinfusion, thereby avoiding periods of deep general anesthesia that compromise the patient's life or periods of sedation which can cause intraoperative awakenings. To avoid overinfusion, restrictions are applied with the safety system (19) to suspend the infusion pump system (2) and to avoid underinfusion, the correction vector (18) is applied.

The SynPID control system (24) uses a quantification system (21) so that the reliable control vector (20) is interpretable by the infusion pump system (2) which, through various catheters, infuse the drugs intravenously in the patient's body (1) modifying the anesthetic state; subsequently, these modifications will be collected by the monitoring equipment (3) by means of the monitoring variable vector (6).

The steps for the multi-infusion of anesthetic drugs with synergy by control in CL MIMO-PID (SynPID) applied in anesthetic acts via IV for automatic infusion, executable in an electronic device, are the following for each moment of action:

Step 1: Measuring the value of the vector of the eBIS (6.1), eNOX (6.2) and eNMB (6.3) monitors, which mainly depends on the infusion vector of the anesthetic ePPF (5.1), eRMF (5.2) and eRCN (5.3) drugs. Anesthetic drugs are administered to the patient (1) by means of an infusion pump system (2). The monitoring equipment (3) collects the effects of the anesthetic drugs on the patient and the surgical actions vector (7) those of the surgeon in a procedure through the monitoring variables vector (6); other factors can influence the value of the monitoring vector. The information of the monitoring variables vector (6) and the decision made on the value of the infusion vector of anesthetic drugs (5) is stored in a memory;

Step 2: Calculating the infusion vector of the anesthetic ePPF (5.1), eRMF (5.2) and eRCN (5.3) drugs by means of a SynPID control system (24) from the feedback of the vector value of the eBIS (6.1), eNOX (6.2) and eNMB (6.3) monitors, of the manual protocol infusion vector relating to the ePPF (4.1), to the eRMF (4.2) and to the eRCN (4.3) and of the vector of the target values of monitored variables relating to eBIS (8.1), to eNOX (8.2) and to eNMB (8.3);

Step 3: Proceed with the cleaning of noise and artifacts of the vector of the eBIS (6.1), eNOX (6.2) and eNMB (6.3) monitors, by means of a cleaning and filtering system for the eBIS (9.1), a cleaning and filtering system for the eNOX (9.2) and a cleaning and filtering system for the eNMB (9.3), to obtain a filtered monitoring variables vector of the eBIS (10.1), eNOX (10.2) and eNMB (10.3);

Step 4: Calculate control error vectors of the monitors to the eBIS (12), eNOX (13) and eNMB (14). The eBIS control error vector has three components: an eBIS proportional asymmetric error (12.1), an eBIS integral symmetric error (12.2), and an eBIS derivative asymmetric error (12.3). The eNOX control error vector has three components: an eNOX proportional asymmetric error (13.1), an eNOX integral symmetric error (13.2), and an eNOX derivative asymmetric error (13.3). The eNMB control error vector has three components: an eNMB proportional asymmetric error (14.1), an eNMB integral symmetric error (14.2), and an eNMB derivative asymmetric error (14.3). The control error vectors (12, 13, 14) are obtained by a control error generator (11) composed of a DoH error generator (28), an ANG error generator (29) and an MRX error generator (30). The DoH error generator (28) obtains the three components, eBIS proportional asymmetric error (12.1), integral symmetric error (12.2) and derivative asymmetric error (12.3), from the filtered monitoring variable of the eBIS (10.1) and the target value of the eBIS (8.1). The ANG error generator (29) obtains the three components, eNOX proportional asymmetric error (13.1), integral symmetric eNOX (13.2) and derivative asymmetric eNOX (13.3) from the filtered monitoring variable of the eNOX (10.2) and the target value of the eNOX (8.2). The MRX error generator (30) obtains the three components eNMB proportional asymmetric error (14.1), eNMB integral symmetric (14.2) and eNMB derivative asymmetric (14.3) from the filtered monitoring variable of the eNMB (10.3) and the target value of the eNMB (8.3). The errors will indicate at the time of their evaluation the deviation of the monitoring variables vector (6) with respect to the vector of objectives of the monitored variables (8).

Step 5: Calculating a drug control infusion vector for ePPF (15.1), eRMF (15.2), and eRCN (15.3) by means of a MIMO-PID synergistic and multi-variable controller (16) that inputs the control error vectors (12, 13, 14) and the manual protocol infusion vector (4). The MIMO-PID multivariable and synergistic controller (16) consists of three MISO-PID control subsystems (25, 26, 27), which in turn each consists of three SISO-PID controllers: 1) SISO-PID controllers (25.1, 25.2, 25.3), used to obtain the ePPF control infusion (15.1); 2) SISO-PID controllers (26.1, 26.2, 26.3), used to obtain the eRMF control infusion (15.2); and 3) SISO-PID controllers (27.1, 27.2, 27.3), used to obtain the eRCN control infusion (15.3).

Step 6: Calculating a correction vector (18) formed by the ePPF corrective infusion (18.1), the eRMF corrective infusion (18.2) and the eRCN corrective infusion (18.3) by an infusion correction system (17) which is formed by an ePPF infusion correction subsystem (17.1), an eRMF infusion correction subsystem (17.2) and an eRCN infusion correction subsystem (17.3) from the filtered monitoring variable vector (10) composed of the eBIS filtered monitoring (10.1), the eNOX filtered monitoring (10.2) and the eNMB filtered monitoring (10.3); the correction vector (18) attempts to compensate the control infusion vector (15) in order to avoid underinfusion to mitigate the effect of the decrease in DoH, ANG and MRX; the correction vector (18) is calculated on the basis of an upper and lower thresholds vector on the filtered variable vector (10);

Step 7: Calculating a reliable control vector (20) formed by the reliable infusion of ePPF (20.1), the reliable infusion of eRMF (20.2) and the reliable infusion of eRCN (20.3) by a safety system (19) which is formed by an ePPF infusion safety subsystem (19.1), an eRMF infusion safety subsystem (19.2) and an eRCN infusion safety subsystem (19.3) from the control infusion vector (15) formed by the ePPF control infusion (15.1), the control infusion of the eRMF (15.2) and the control infusion of the eRCN (15.3) and from the correction vector (18) formed by the corrective infusion of ePPF (18.1), the corrective infusion of eRMF (18.2) and the corrective infusion of eRCN (18.3); the safety system (19) attempts to compensate the control infusion vector (15) to drive the reliable control vector (20) to a reliable value for the patient (1) and reliable to cause the desired effect on the patient (1), which prevents overinfusion and underinfusion, thereby avoiding periods of deep general anesthesia that compromises the patient's life or periods of sedation which can cause intraoperative awakenings; to avoid overinfusion, suspension restriction vectors of the infusion pump system are applied (2) and to avoid underinfusion, the correction vector (18) is applied;

Step 8: Calculating an automatic infusion vector (22) formed by the automatic infusion of ePPF (22.1), the automatic infusion of eRMF (22.2) and the automatic infusion of eRCN (22.3) by a quantification system (21) which is formed by an infusion quantification subsystem of the ePPF (21.1), an infusion quantification subsystem of the eRMF (21.2) and an infusion quantification subsystem of the eRCN (21.3) from a reliable control vector (20) formed by the reliable infusion of ePPF (20.1), the reliable infusion of eRMF (20.2) and the reliable infusion of eRCN (20.3); the quantification system (21) modifies the infusions so that the reliable control vector (20) is interpretable by the infusion pump system (2), composed of the ePF pump (2.1), the eRMF pump (2.2) and the eRCN pump (2.3), which infuse the drug through various IV catheters to the patient (1);

Step 9: Defining the anesthetic drug infusion vector (5) composed of the ePPF infusion (5.1), the eRMF infusion (5.2) and the eRCN infusion (5.3) by a switching system (23) to control the time elapsed in IPh, the time in MPh and the time in RPh; in IPh the anesthetic drug infusion vector (5) is the same as the manual protocol infusion vector (4); in MPh the anesthetic drug infusion vector (5) is the same as the automatic infusion vector (22); and in RPh the suspension of the infusion pump system (2) is activated;

Step 10: Calculating the control infusion of the ePPF drug (15.1) from the MISO-PID-ePPF $C_1$ control subsystem (25), which in turn is formed by three SISO-PID controllers ($C_{11}$, $C_{12}$, $C_{13}$) (25.1, 25.2, 25.3), each SISO-PID controller in turn formed by three drug control actions that are detailed below: 1) the SISO-PID CD controller (25.1) that calculates the contribution to the infusion of the ePPF drug infusion (15.1.1)

provided by the eBIS monitor control error vector (12), is formed by a proportional action that relates the partial infusion of ePPF (15.1.1.1) to the proportional control asymmetric error relative to the eBIS (12.1), by an integral action that relates the partial infusion of ePPF (15.1.1.2) to the integral control symmetric error relative to the eBIS (12.2) and by a derivative action that relates the partial infusion of ePPF (15.1.1.3) to the derivative asymmetric error relative to eBIS (12.3); 2) the SISO-PID $C_{72}$ controller (25.2) that calculates the contribution to the control infusion of the ePPF drug infusion (15.1.2) provided by the control error vector of the eNOX monitor (13) is formed by a proportional action that relates the partial infusion of ePPF (15.1.2.1) to the asymmetric error of proportional control relative to the eNOX (13.1), by an integral action that relates the partial infusion of ePPF (15.1.2.2) to the integral control symmetric error relative to eNOX (13.2) and by a derivative action that relates the partial infusion of ePPF (15.1.2.3) to the derivative asymmetric error relative to eNOX (13.3); 3) the SISO-PID $C_{I3}$ controller (25.3) that calculates the contribution to the control infusion of the ePPF drug infusion (15.1.3) provided by the control error vector of the eNMB monitor (14) is formed by a proportional action that relates the partial infusion of ePPF (15.1.3.1) to the proportional control asymmetric error relative to eNMB (14.1), by an integral action that relates the partial infusion of ePPF (15.1.3.2) to the integral control symmetric error relative to eNMB (14.2) and by a derivative action that relates the partial infusion of ePF (15.1.3.3) to the derivative asymmetric error relative to the eNMB (14.3);

Step 11: Calculating the control infusion of the eRMF drug (15.2) from the MISO-PID-eRMF $C_2$ control subsystem (26), which in turn is formed by three SISO-PID controllers ($C_{21}, C_{22}, C_{23}$) (26.1, 26.2, 26.3), each SISO-PID controller in turn formed by three drug control actions that are detailed below: 1) the SISO-PID $C_{21}$ controller (26.1) that calculates the contribution to the control infusion of the eRMF drug infusion (15.2.1) provided by the control error vector of the eBIS monitor (12), is formed by a proportional action that relates the partial infusion of ePPF (15.2.1.1) to the asymmetric error of proportional control relative to the eBIS (12.1), by an integral action that relates the partial infusion of eRMF (15.2.1.2) to the symmetric error of integral control relative to the eBIS (12.2) and by a derivative action that relates the partial infusion of eRMF (15.2.1.3) to the derivative asymmetric error relating to eBIS (12.3); 2) the SISO-PID $C_{22}$ controller (26.2) that calculates the contribution to the control infusion of the eRMF drug infusion (15.2.2) provided by the control error vector of the eNOX monitor (13) is formed by a proportional action that relates the partial infusion of eRMF (15.2.2.1) to the asymmetric error of proportional control relating to eNOX (13.1), by an integral action that relates the partial infusion of eRMF (15.2.2.2) to the integral control symmetric error relating to eNOX (13.2) and by a derivative action that relates the partial infusion of eRMF (15.2.2.3) to the derivative asymmetric error relating to eNOX (13.3); 3) the SISO-PID $C_{23}$ controller (26.3) that calculates the contribution to the control infusion of the eRMF drug infusion (15.2.3) provided by the eNMB monitor control error vector (14), is formed by a proportional action that relates the partial infusion of eRMF (15.2.3.1) to the proportional control asymmetric error relating to eNMB (14.1), by an integral action that relates the partial infusion of eRMF (15.2.3.2) to the integral control symmetric error relating to eNMB (14.2) and by a derivative action that relates the partial infusion of eRMF (15.2.3.3) to the derivative asymmetric error relating to eNMB (14.3);

Step 12: Calculating the control infusion of the eRCN drug (15.3) from the MISO-PID-eNMB $C_3$ control subsystem (27), which in turn is formed by three SISO-PID controllers ($C_{31}, C_{32}, C_{33}$) (27.1, 27.2, 27.3), each SISO-PID controller is in turn formed by three drug control actions that are detailed below: 1) the SISO-PID $C_{37}$ controller (27.1) that calculates the contribution to the control infusion of the eRCN drug infusion (15.3.1) provided by the control error vector relative to the eBIS (12) is formed by a proportional action that relates the partial infusion of eRCN (15.3.1.1) to the proportional control asymmetric error relative to the eBIS (12.1), by an integral action that relates the partial infusion of eRCN (15.3.1.2) to the integral control symmetric error relative to the eBIS (12.2) and by a derivative action that relates the partial infusion of eRCN (15.3.1.3) to the derivative asymmetric error relative to the eBIS (12.3); 2) the SISO-PID $C_{32}$ controller (27.2) that calculates the contribution to the control infusion of the eRCN drug infusion (15.3.2) provided by the control error vector of the eNOX monitor (13), is formed by a proportional action that relates the partial infusion of eRCN (15.3.2.1) to the asymmetric error of proportional control relative to the eNOX (13.1), by an integral action that relates the partial infusion of eRCN (15.3.2.2) to the integral control symmetric error relative to the eNOX (13.2) and by a derivative action that relates the partial infusion of eRCN (15.3.2.3) to the derivative asymmetric error relative to the eNOX (13.3); 3) the SISO-PID $C_{33}$ controller (27.3) that calculates the contribution to the control infusion of the eRCN drug infusion (15.3.3) provided by the control error vector relative to eNMB (14), is formed by a proportional action that relates the partial infusion of eRMF (15.3.3.1) to the proportional control asymmetric error relative to the eNMB (14.1), by an integral action that relates the partial infusion of eRCN (15.3.2) to the integral control symmetric error relative to the eNMB (14.2) and by a derivative action that relates the partial infusion of eRCN (15.3.3.3) to the derivative asymmetric error relative to the eNMB (14.3.3);

Next, the equations are expressed that define the SynPID control system which, using the manual protocol infusion vector (4), the monitoring variables vector (6), the vector of objectives of the monitored variables (8), the vectors of control errors (12, 13, 14), the correction vector (18) and the reliable control vector (20), obtains an anesthetic drug infusion vector (5) that will keep the patient (1) in a satisfactory anesthetic state despite surgery. The drugs considered are ePPF, eRMF and eRCN and the monitors considered are eBIS, eNOX and eNMB, so the order of the vectors is fixed at 3×1 and the order of the matrices at 3×3, in this exemplary embodiment of the invention. It should be noted that the present invention does not make use of pharmacokinetic or pharmacodynamic models for its design or for personalization to each patient (1).

Before detailing the method and in order to clarify the variables that appear in the equations, the most important ones grouped by their physical units and common characteristics are listed below:

1) The dimensions of the multivariable system are 3×3, relative to the monitoring variables vector (6) r=3, where 1 refers to the eBIS, 2 refers to the eNOX and 3 refers to the eNMB; and relative to the anesthetic drug infusion vector (5) s=3, where 1 refers to the ePPF, 2 refers to the eRMF and 3 refers to the eRCN;

2) The discrete time is represented with the integer k, so that a real time t, can be shown as: t=k·T$_s$–, where T$_s$ is the infusion period; the IPh start time is t$_i$, the MPh start time is t$_m$ and the RPh start time is t$_r$.

3) Vectors that refer to drug infusions, infusion units 15 per patient weight [µg (min kg)], general equation:

$$u_x[u_{x1}\ u_{x2}\ u_{x3}]^T,$$

Where u$_x$ refers to the infusion column vector with dimension (3×1); u$_{x1}$ is the infusion of the ePPF; u$_{x2}$ is the infusion of the eRMF; u$_{x3}$ is the infusion of the eRCN; and T indicates the transposition of the vector.

The list of infusion variables is as follows:

| X | Ref. | Infusion Vector | Symbol | Eq. |
|---|------|-----------------|--------|-----|
| ol | 4 | Manual protocol (OL) | $u_{ol}$ | [2.2] |
| pt | 5 | of anesthetic drugs | $u_p$ | |
| pid | 15 | of drug control | $u_{pid}$ | [5.1] |
| cr | 18 | drug corrector | $u_{cr}$ | [6.1] |
| sf | 20 | reliable drug delivery | $u_{sf}$ | [7.1] |
| HI | | of upper limit | $u_{HI}$ | [7.3] |
| LO | | of lower limit | $u_{LO}$ | [7.4] |
| cl | 22 | automatic in CL | $u_{cl}$ | [8.1] |
| mn | | resolution of pumps | $u_{mn}$ | [8.3] | x: refers to the subscript of the vector considered; Ref. Indicates the number that appears in the figures; Symbol: Identifies the variable by its name; Eq. Indicates the equation of the general description where it has been defined.

4) Vectors that refer to the monitoring variables, monitoring units (UM) and the range of variation is from 0 to 100; general equation:

$$y_z=[y_{z1} y_{z2} y_{z3}]^T,$$

Where y$_z$ refers to the column vector monitoring variables (3×1); y$_{z1}$ is eBIS monitoring; y$_{z2}$ is eNOX monitoring; y$_{z3}$ is eNMB monitoring; T indicates vector transposition.

The list of monitoring variables and their variants is as follows:

| z | Ref. | Description of vector of | Symbol | Eq. |
|---|------|--------------------------|--------|-----|
| | 6 | measured monitoring variables | y | [2.1] |
| T | 8 | target values of the monitored variables | $y_T$ | [2.6] |
| f | 10 | filtered monitoring variables | $y_f$ | [3.1] |
| HI | | upper thresholds for the activation of the correction | $y_{HI}$ | [6.3] |
| LO | | lower thresholds for the activation of the correction | $y_{LO}$ | [6.4] | z: refers to the subscript of the vector considered; Ref. indicates the number that appears in the figures; Symbol: Identifies the variable by its name; Eq. indicates the equation of the general description where it has been defined.

5) Vectors referring to the vectors of control errors (12, 13, 14), with variation range ±200 UM; general equation:

$$e_j=[e_{Pj} e_{Ij} e_{Fj}]^T,$$

Where e$_1$ refers to the control error column vector (3×1); e$_1$ is the control error vector relative to the eBIS; e$_2$ is the control error vector relative to the eNOX; 15 e$_3$ is the control error vector relative to the eNMB; e$_{Pi}$ is the proportional control asymmetric error vector relative to the monitor y; e$_{ii}$ is the integral control symmetric error vector relative to the monitor y; and e$_{Fi}$ is the derivative control asymmetric and filtering error vector relative to the monitor y; T indicates the vector transposition.

The list of error variables and their variants is as follows:

| j | Ref. | Description of the control error | Symbol | Eq. |
|---|------|----------------------------------|--------|-----|
| 1 | 12 | eBIS vector | $e_1$ | [4.1] |
| 1 | 12.1 | eBIS proportional asymmetric component | $e_{P1}$ | [4.2] |
| 1 | 12.2 | eBIS integral symmetric component | $E_{I1}$ | |
| 1 | 12.3 | eBIS filtered derivative asymmetric component | $e_{F1}$ | |
| 2 | 13 | eNOX vector | $e_2$ | [4.1] |
| 2 | 13.1 | proportional asymmetric component related to eNOX | $e_{P1}$ | [4.2] |
| 2 | 13.2 | integral symmetrical component relating to eNOX | $E_{I1}$ | |
| 2 | 13.3 | filtered derivative asymmetric component related to eNOX | $e_{F1}$ | |
| 3 | 14 | eNMB vector | $e_3$ | [4.1] |
| 3 | 14.1 | eNMB proportional asymmetric component | $e_{P1}$ | [4.2] |
| 3 | 14.2 | eNMB integral symmetric component | $e_{I1}$ | |
| 3 | 14.3 | filtered derivative asymmetric component relating to the eNMB | $e_{D1}$ | | j: refers to the subscript of the vector considered; Ref. indicates the number that appears in the figures; Symbol: Identifies the variable by its name; Eq. indicates the equation of the general description where it has been defined.

6) Variables that refer to the multivariable and synergistic MIMO-PID controller (16); to the MISO-PID control subsystems (25, 26, 27) and to the SISO-PID controllers.

$$[PID] = \begin{bmatrix} C_1 \\ C_2 \\ C_3 \end{bmatrix} = \begin{bmatrix} C_{11} & C_{12} & C_{13} \\ C_{21} & C_{22} & C_{23} \\ C_{31} & C_{32} & C_{33} \end{bmatrix},$$

Where [PID] is the array of PID controllers that make up the MIMO-PID multivariable and synergistic controller (16); C$_1$ is the vector of PID controllers that make up the MISO-PID-ePPF control subsystem (25); C$_2$ is the vector of PID controllers that make up the MISO-PID-eRMF control subsystem (26); C$_3$ is the vector of PID controllers that make up the MISO-PID-eNMB control subsystem (27); C$_{ij}$ is the SISO-PID controller that relates the error associated with the monitor i to the drug j.

| i, j | Ref. | PID Controller Description | Symbol | Eq. |
|------|------|---------------------------|--------|-----|
| 1 | 25 | MISO: ePPF → eBIS, eNOX, eNMB | $C_1$ | [5.3] |
| 1.1 | 25.1 | SISO: ePPF → eBIS | $C_{11}$ | |
| 1.2 | 25.2 | SISO: ePPF → eNOX | $C_{12}$ | |
| 1.3 | 25.3 | SISO: ePPF → eNMB | $C_{13}$ | |
| 2 | 26 | MISO: eRMF → eBIS, eNOX, eNMB | $C_2$ | |
| 2.1 | 26.1 | SISO: eRMF → eBIS | $C_{21}$ | |
| 2.2 | 26.2 | SISO: eRMF → eNOX | $C_{22}$ | |
| 2.3 | 26.3 | SISO: eRMF → eNMB | $C_{23}$ | |
| 3 | 27 | MISO: eRCN → eBIS, eNOX, eNMB | $C_3$ | |
| 3.1 | 27.1 | SISO: eRCN → eBIS | $C_{31}$ | |
| 3.2 | 27.2 | SISO: eRCN → eNOX | $C_{32}$ | |
| 3.3 | 27.3 | SISO: eRCN → eNMB | $C_{33}$ | | i, j: refers to the subscript(s) of the controller(s) considered; Ref. indicates the number that appears in the figures; Symbol: Identifies the variable by its name; Eq. indicates the equation of the general description where it has been defined.

The system of the present invention is updated every T$_s$ seconds, the time associated with the sampling period. The system starts at time t$_i$ with the IPh. From the moment of switching from the IPh to the MPh ($t_m$) the values are updated each period of execution of the method ($T_s$) according to equations 2 to 13, as detailed below:

Equation 2: Measure the monitoring variables vector (6); define and calculate the vector of infusions of the manual protocol (4); and set the vector of objectives of the monitored variables (8). These are the results obtained in step 2.

| Ref. | Mathematical Definition | Eq. |
|---|---|---|
| 6 | $y = [y_1 \quad y_2 \quad y_3]^T,$ | [2.1] |
| 4 | $u_{ol} = [u_{ol1} \quad u_{ol2} \quad u_{ol3}]^T,$ | [2.2] |
| | $u_{ol}(t) = d(t_i) + r_{ol}(t),$ | [2.3] |
| | $d(t_i) = \dfrac{D \cdot W}{T_s},$ | [2.4] |
| | $D = [D_1 \quad D_2 \quad D_3]^T,$ | |
| | $r_{ol}(t) = \begin{cases} R \cdot W, & t_i \leq t < t_m \\ R \cdot W - P \cdot (t - t_m), & t_m \leq t < t_r \end{cases},$ | [2.5] |
| | $R = [R_1 \quad R_2 \quad R_3]^T,$ | |
| | $P = [P_1 \quad P_2 \quad P_3]^T,$ | |
| 8 | $y_T = [y_{T1} \quad y_{T2} \quad y_{T3}]^T,$ | [2.6] |

Ref indicates the number that appears in the figures; Eq. indicates the equation of the general description where it has been defined, particularized for s=r=3.

Equation 3: Calculate the filtered monitoring variables vector (10), define a 5 filter bank (9) based on low-pass filters of order 1; and define a cut-off frequency vector. The result of step 3 is the filtered monitoring variables vector (10).

| Ref. | Mathematical Definition | Eq. |
|---|---|---|
| 10 | $y_f = [y_{f1} \quad y_{f2} \quad y_{f3}]^T,$ | [3.1] |
| 9 | $H(f) = \dfrac{1}{1 + \dfrac{j \cdot f}{f_c}},$ | [3.2] |
| | $f_c = [f_1 \quad f_2 \quad f_3]^T$ | [3.3] |
| | $f_c = \dfrac{N}{T_D},$ | [3.4] |

Ref. indicates the number that appears in the figures; Eq. indicates the equation of the general description where it has been defined, particularized for s = r = 3.

Equation 4: Calculate the eBIS $e_1$ monitor control error vector (12) with the DoH error generator (28), the eNOX $e_2$ monitor control error vector (13) with the ANG error generator (29), and the 15 eNMB $e_3$ monitor control error vector (14) with the RMX error generator (30), each with its proportional, integral and derivative components (12.1, 12.2, 12.3), (13.1, 13.2, 13.3) and (14.1, 14.2, 14.3); calculate the proportional asymmetric (12.1, 13.1, 14.1), integral symmetric (12.2, 13.2, 14.2) and derivative asymmetric (12.3, 13.3, 14.3) errors of each SISO-PID controller. The asymmetric errors shown in the present invention are calculated in such a way that the target vector of the monitored variables (8) is weighted by an array of coefficients [B] in the proportional action and an array of coefficients [G] in the derivative action, the weighting value of the integral action being unitary. The SynPID control system of the present invention is defined by both [B] and [G] dependent on the monitoring variables vector (6) and the vector of targets of the monitored variables (8). The results of step 4 are the control error vectors (12, 13, 14).

| Ref. | Mathematical Definition | Eq. |
|---|---|---|
| 12 | $e_1 = [e_{P1} \quad e_{I1} \quad e_{F1}]^T$ | [4.1] |
| 13 | $e_2 = [e_{P2} \quad e_{I2} \quad e_{F2}]^T$ | |
| 14 | $e_3 = [e_{P3} \quad e_{I3} \quad e_{F3}]^T$ | |
| 37 | $e_{P1} = -\beta_{11} \cdot y_{T1} + y_{f1}$ | [4.2] |
| | $e_{I1} = -y_{T1} + y_{f1}$ | [4.7] |
| | $e_{D1} = -\gamma_{11} \cdot y_{T1} + y_{f1}$ | |
| | $e_{F1} = e_{D1} - \dfrac{T_{D11}}{N} \dfrac{de_{F1}}{dt}$ | |
| 38 | $e_{P2} = -\beta_{22} \cdot y_{T2} + y_{f2}$ | [4.2] |
| | $e_{I2} = -y_{T2} + y_{f2}$ | [4.8] |
| | $e_{D2} = -\gamma_{22} \cdot y_{T2} + y_{f2}$ | |
| | $e_{F2} = e_{D2} - \dfrac{T_{D22}}{N} \dfrac{de_{F2}}{dt}$ | |
| 39 | $e_{P3} = -\beta_{33} \cdot y_{T3} + y_{f3}$ | [4.2] |
| | $e_{I3} = -y_{T3} + y_{f3}$ | [4.9] |
| | $e_{D3} = -\gamma_{33} \cdot y_{T3} + y_{f3}$ | |
| | $e_{F3} = e_{D3} - \dfrac{T_{D33}}{N} \dfrac{de_{F3}}{dt}$ | |
| | $\beta = \begin{cases} \dfrac{-y_f - y_{thb}}{y_T - y_{thb}} + 2, & y_f < y_T \\ 1, & y_f \geq y_T \end{cases}$ | [4.4] |
| | $\gamma = \begin{cases} \dfrac{-y_f - y_{thg}}{y_T - y_{thg}} + 2, & y_f < y_T \\ 1, & y_f \geq y_T \end{cases}$ | [4.6] |
| | $y_{thb} = [y_{thb1} \quad y_{thb2} \quad y_{thb3}]^T$ | |
| | $y_{thg} = [y_{thg1} \quad y_{thg2} \quad y_{thg3}]^T$ | |

Ref. indicates the number that appears in the figures; Eq. indicates the equation of the general description where it has been defined, particularized for s = r = 3.

Equation 5: Calculate the control infusion vector (15) by means of a multivariable and MIMO-PID-synergized controller (16), the control error vectors of the eBIS monitor (12), eNOX (13) and eNMB (14) and the manual protocol infusion vector (4); define the [PID] matrix of SISO-PID controllers that make up the multivariable and MIMO-PID-synergized controller (16); define the SISO-PID Cu controllers relative to the j monitor and the drug i; define the proportional, integral and derivative control actions of the SISO-PID controllers whose sum defines the total control action of each SISO-PID controller; define the gain matrices relative to the SISO-PID controllers; define the drug synergy matrix; define the $K_{ol}$ gain vector on the manual protocol infusion vector (4); define the MISO-PID control subsystems (25, 26, 27). The result of Step 5 is the control infusion vector (15).

| Ref. | Mathematical Definition | Eq. |
|---|---|---|
| 15 | $u_{pid} = [u_1 \quad u_2 \quad u_3]^T$ | [5.1] |
| | $u_{pid} = [PID] \cdot [SYN] + K_{ol} \cdot u_{ol}$ | [5.2] |
| 16 | $[PID] = \begin{bmatrix} C_{11} & C_{12} & C_{13} \\ C_{21} & C_{22} & C_{23} \\ C_{31} & C_{32} & C_{33} \end{bmatrix} = \begin{bmatrix} C_1 \\ C_2 \\ C_3 \end{bmatrix}$ | [5.3] |
| | $C_{ij} = P_{ij} + I_{ij} + D_{ij}$ | [5.14] |
| | $P_{ij} = K_{Pij} \cdot e_{Pj}$ | [5.15] |
| | $I_{ij} = K_{Iij} \int e_{Ij} d\tau$ | |
| | $D_{ij} = K_{Dij} \dfrac{de_{Fj}}{dt}$ | |

-continued

| Ref. | Mathematical Definition | Eq. |
|---|---|---|
| | $$[K_P] = \begin{bmatrix} K_{P11} & K_{P12} & \dots & K_{P1r} \\ K_{P21} & K_{P22} & \dots & K_{P2r} \\ \vdots & \vdots & \ddots & \vdots \\ K_{Ps1} & K_{Ps2} & \dots & K_{Psr} \end{bmatrix} = \begin{bmatrix} K_{P1} \\ K_{P1} \\ \vdots \\ K_{Ps} \end{bmatrix}$$ | [5.4] |
| | $$[K_I] = \begin{bmatrix} K_{I11} & K_{I12} & \dots & K_{I1r} \\ K_{I21} & K_{I22} & \dots & K_{I2r} \\ \vdots & \vdots & \ddots & \vdots \\ K_{Is1} & K_{Is2} & \dots & K_{Isr} \end{bmatrix} = \begin{bmatrix} K_{I1} \\ K_{I2} \\ \vdots \\ K_{Is} \end{bmatrix}$$ | [5.5] |
| | $$[K_D] = \begin{bmatrix} K_{D11} & K_{D12} & \dots & K_{D1r} \\ K_{D21} & K_{D22} & \dots & K_{D2r} \\ \vdots & \vdots & \ddots & \vdots \\ K_{Ds1} & K_{Ds2} & \dots & K_{Dsr} \end{bmatrix} = \begin{bmatrix} K_{D1} \\ K_{D2} \\ \vdots \\ K_{Ds} \end{bmatrix}$$ | [5.6] |
| | $K_P = \mathrm{diag}([K_P])$ | [5.7] |
| | $K_I = \mathrm{diag}([K_I])$ | [5.8] |
| | $K_D = \mathrm{diag}([K_D])$ | [5.9] |
| | $$[SYN] = \begin{bmatrix} S_{11} & S_{12} & \dots & S_{1r} \\ S_{21} & S_{22} & \dots & S_{2r} \\ \vdots & \vdots & \ddots & \vdots \\ S_{s1} & S_{s2} & \dots & S_{sr} \end{bmatrix}^T = \begin{bmatrix} S_1 \\ S_2 \\ \vdots \\ S_s \end{bmatrix}^T$$ | [5.10] |
| | $K_{o1} = [K_{o l1} \quad K_{o l2} \quad K_{o l3}]^T$ | [5.11] |
| | $$K_{ol} = \begin{cases} 1, & y_T \le y_f, \\ \dfrac{y_f}{y_T - y_{LO}} - \dfrac{y_{LO}}{y_T - y_{LO}}, & y_{LO} \le y_f \le y_T, \\ 0, & \text{otherwise,} \end{cases}$$ | [5.12] |
| 25 | $u_1 = C_{11} \cdot S_{11} + C_{12} \cdot S_{12} + C_{13} \cdot S_{13} + K_{o l1}\, u_{o l1}$ <br> $C_1 = [C_{11} \quad C_{12} \quad C_{13}]$ | [5.13] |
| 26 | $u_2 = C_{21} \cdot S_{21} + C_{22} \cdot S_{22} + C_{23} \cdot S_{23} + K_{o l2}\, u_{o l2}$ <br> $C_2 = [C_{21} \quad C_{22} \quad C_{23}]$ | |
| 27 | $u_3 = C_{31} \cdot S_{31} + C_{32} \cdot S_{32} + C_{33} \cdot S_{33} + K_{o l3}\, u_{o l3}$ <br> $C_3 = [C_{31} \quad C_{32} \quad C_{33}]$ | |

Ref. indicates the number that appears in the figures; Eq. indicates the equation of the general description where it has been defined, particularized for s = r = 3.

Equation 6: Define and calculate drug corrective infusions (18) from the filtered monitoring variables vector (10); define the vectors of the upper and lower thresholds of activation of the correction. The result of step 6 is the correction vector (18).

| Ref. | Mathematical Definition | Eq. |
|---|---|---|
| 18 | $u_{cr} = [u_{cr1} \quad u_{cr2} \quad u_{cr3}]^T$ | [6.1] |
| 17 | $$u_{cr} = \begin{cases} K_P^T \cdot [SYN] \cdot [-y_m + y_f] & y_{HI} \le y_f \\ K_P^T \cdot [SYN] \cdot [-y_{LO} + y_f] & y_{LO} \ge y_f \\ 0, & \text{otherwise} \end{cases}$$ | [6.2] |
| 18.1 | $$u_{cr1} = \begin{cases} K_{P1}^T \cdot [S_1] \cdot [-y_{HI} + y_f] & y_{HI} \le y_f \\ K_{P1}^T \cdot [S_1] \cdot [-y_{LO} + y_f] & y_{LO} \ge y_f \\ 0, & \text{otherwise} \end{cases}$$ | |
| 18.2 | $$u_{cr2} = \begin{cases} K_{P2}^T \cdot [S_2] \cdot [-y_{HI} + y_f] & y_{HI} \le y_f \\ K_{P2}^T \cdot [S_2] \cdot [-y_{LO} + y_f] & y_{LO} \ge y_f \\ 0, & \text{otherwise} \end{cases}$$ | |
| 18.3 | $$u_{cr3} = \begin{cases} K_{P3}^T \cdot [S_3] \cdot [-y_{HI} + y_f] & y_{HI} \le y_f \\ K_{P3}^T \cdot [S_3] \cdot [-y_{LO} + y_f] & y_{LO} \ge y_f \\ 0, & \text{otherwise} \end{cases}$$ | |

-continued

| Ref. | Mathematical Definition | Eq. |
|---|---|---|
| | $y_{HI} = [H_1 \quad H_2 \quad H_3]^T$ | [6.3] |
| | $y_{LO} = [L_1 \quad L_2 \quad L_3]^T$ | [6.4] |

Ref. indicates the number that appears in the figures; Eq. indicates the equation of the general description where it has been defined, particularized for s = r = 3.

Equation 7: Define and calculate the reliable control vector (20), to avoid the over/under dosing of drugs, from the control infusion vector (15) and the correction vector (18); define the vectors of upper and lower limits of the drug infusion according to two concepts: 1) only positive infusions can be applied to the patient (1), therefore, the infusion pump system (2) is suspended (null infusion) when the control infusion vector (15) plus the correction vector (18) results in negative or null infusions; and 2) maximum infusion limits should avoid drug overdoses to avoid toxicity levels. The result of step 7 is the reliable control vector 20.

| Ref. | Mathematical Definition | Eq. |
|---|---|---|
| 20 | $u_{sf} = [u_{sf1} \quad u_{sf2} \quad u_{sf3}]^T$ | [7.1] |
| 19 | $$u_{sf} = \begin{cases} u_{HI}, & u_{pid} + u_{cr} \ge u_{HI} \\ u_{pid} + u_{cr}, & u_{LO} < u_{pid} + u_{cr} \le u_{HI} \\ u_{LO}, & u_{pid} + u_{cr} \le u_{LO} \end{cases}$$ | [7.2] |
| 20.1 | $$u_{sf1} = \begin{cases} u_{H1}, & u_1 + u_{cr1} \ge u_{H1} \\ u_1 + u_{cr1}, & u_{L1} < u_1 + u_{cr1} \le u_{H1} \\ u_{L1}, & u_1 + u_{cr1} \le u_{L1} \end{cases}$$ | |
| 20.2 | $$u_{sf2} = \begin{cases} u_{H2}, & u_2 + u_{cr2} \ge u_{H2} \\ u_2 + u_{cr2}, & u_{L2} < u_2 + u_{cr2} \le u_{H2} \\ u_{L2}, & u_2 + u_{cr2} \le u_{L2} \end{cases}$$ | |
| 20.3 | $$u_{sf3} = \begin{cases} u_{H3}, & u_3 + u_{cr3} \ge u_{H3} \\ u_3 + u_{cr3}, & u_{L3} < u_3 + u_{cr3} \le u_{H3} \\ u_{L3}, & u_3 + u_{cr3} \le u_{L3} \end{cases}$$ | |
| | $u_{HI} = [u_{H1} \quad u_{H2} \quad u_H]^T$ | [7.3] |
| | $u_{LO} = [u_{L1} \quad u_{L2} \quad u_{L3}]^T$ | [7.4] |

Ref. indicates the number that appears in the figures; Eq. indicates the equation of the general description where it has been defined, particularized for s = r = 3.

Equation 8: Define and calculate the automatic infusion vector (22) from the reliable control vector (20); define the resolution vector of each drug infusion pump; the reliable control vector (20) is adapted to the resolution of the continuous infusion pump system (2) to thereby obtain the automatic infusion vector (22) that is dispensed to the patient (1). The result of step 8 is the automatic infusion vector 22.

| Ref. | Mathematical Definition | Eq. |
|---|---|---|
| 22 | $u_{c1} = [u_{c l1} \quad u_{c l2} \quad u_{c l3}]^T$ | [8.1] |
| 21 | $u_{cl} = \mathrm{round}\left(\dfrac{u_{sf}}{u_{mn}}\right) \cdot u_{mn}$ | [8.2] |
| 22.1 | $u_{cl1} = \mathrm{round}\left(\dfrac{u_{sf1}}{u_{mn1}}\right) \cdot u_{mn1}$ | |
| 22.2 | $u_{cl2} = \mathrm{round}\left(\dfrac{u_{sf2}}{u_{mn2}}\right) \cdot u_{mn2}$ | |

-continued

| Ref. | Mathematical Definition | Eq. |
|---|---|---|
| 22.3 | $u_{c/3} = \text{round}\left(\dfrac{u_{sf3}}{u_{mn3}}\right) \cdot u_{mn3}$ | |
| | $u_{mn} = [u_{mn1} \quad u_{mn2} \quad u_{mn3}]^T$ | [8.3] |

Ref. indicates the number that appears in the figures; Eq. indicates the equation of the general description where it has been defined, particularized for s = r = 3.

Equation 9: Define and calculate the anesthetic drug infusion vector (5) from the manual protocol infusion vector (4) and the automatic infusion vector (22) from a switching system (23). The result of step 9 is the anesthetic drug infusion vector (5).

| Ref. | Mathematical Definition | Eq. |
|---|---|---|
| 25 | $C_1 = [C_{11}\,C_{12}\,C_{13}]^T$ | [10.1] |
| 15.1 | $u_1 = C_1 \cdot S_1 + K_{o/1} \cdot u_{o/1}$ | [10.2] |
| | $u_1 = C_{11} \cdot S_{11} + C_{12} \cdot S_{12} + C_{13} \cdot S_{13} + K_{o/1}\,u_{o/1}$ | |

Ref. indicates the number that appears in the figures; Eq. indicates the equation of the general description where it has been defined, particularized for s = r = 3.

Equation 10: Define the MISO-PID-ePPF control subsystem (25) as a set of SISO-PID controllers; calculate the control infusion of the ePPF (15.1); from the SISO-PID controllers (25.1, 25, 0.2, 25.3), from the control error vectors (12, 13, 14) and from the infusion of ePPF of the manual protocol (4.1). The result of step 10 is the ePPF control infusion (15.1).

| Ref. | Mathematical Definition | Eq. |
|---|---|---|
| 25 | $C_1 = [C_{11}\,C_{12}\,C_{13}]^T$ | [10.1] |
| 15.1 | $u_1 = C_1 \cdot S_1 + K_{o/1} \cdot u_{o/1}$ | [10.2] |
| | $u_1 = C_{11} \cdot S_{11} + C_{12} \cdot S_{12} + C_{13} \cdot S_{13} + K_{o/1}\,u_{o/1}$ | |

Ref. indicates the number that appears in the figures; Eq. indicates the equation of the general description where it has been defined, particularized for s = r = 3.

Equation 11: Define the MISO-PID-eRMF control subsystem (26) as a set of SISO-PID controllers; calculate the control infusion of the eRMF (15.2); from the SISO-PID controllers (26.1, 26, 0.2, 26.3), from the control error vectors (12, 13, 14) and from the infusion of ePPF of the manual protocol (4.2). The result of step 11 is the control infusion of the eRMF (15.2).

| Ref. | Mathematical Definition | Eq. |
|---|---|---|
| 26 | $C2 = [C_{21}\,C_{22}\,C_{23}]^T$ | [11.1] |
| 15 | $U_2 = C_2 \cdot S_2 + K_{o/2}\,u_{o/2}$ | [11.2] |
| | $u_2 = C_{21} \cdot S_{21} + C_{22} \cdot S_{22} + C_{23} \cdot S_{23} + K_{o/2}\,u_{o/2}$ | |

Ref. indicates the number that appears in the figures; Eq. indicates the equation of the general description where it has been defined, particularized for s = r = 3.

Equation 12: Define the MISO-PID-eNMB control subsystem (27) as a set of SISO-PID controllers; calculate the control infusion of the eRCN (15.3); from the SISO-PID controllers (27.1, 27, 0.2, 27.3), from the control error vectors (12, 13, 14) and from the infusion of eRCN of the manual protocol (4.3). The result of step 11 is the eRCN control infusion (15.3).

| Ref. | Mathematical Definition | Eq. |
|---|---|---|
| 27 | $C_3 = [C_{31}\,C_{32}\,C_{33}]^T$ | [10.1] |
| 15.3 | $u_3 = C_3 \cdot S_3 + K_{o/3} \cdot u_{o/3}$ | [10.2] |
| | $u_3 = C_{31} \cdot S_{31} + C_{32} \cdot S_{32} + C_{33} \cdot S_{33} + K_{o/3} \cdot u_{o/3}$ | |

Ref. indicates the number that appears in the figures; Eq. indicates the equation of the general description where it has been defined, particularized for s = r = 3.

Equation 13: It is formulated for the claiming of new drugs and monitors.

| Ref. | Mathematical Definition | Eq. |
|---|---|---|
| | $C_i = [C_{i1}\,C_{i2}\,\ldots\,C_{ir}]^T$ | [13.1] |
| | $u_i = C_i \cdot S_i + K_{o/i} \cdot u_{o/i}$ | [13.2] |

Ref. indicates the number that appears in the figures; Eq. indicates the equation of the general description where it has been defined, particularized for s = r = 3.

Equation 14: Adjustment of the parameters of the SynPID control system to each patient to absorb inter/intra-patient variability. The adjustment involves step 3 and step 5 of the invention. In step 3 the cut-off frequencies of the filters expressed in the equations [3.5] and [3.6] have to be adjusted. In step 5, the MIMO-PID (16) multivariable and synergistic controller gain matrices expressed in the equations [5.16], [5.17] and [5.18] have to be adjusted.

The information necessary for the adjustment is extracted in the IPh where the patient (1) is subjected only to the manual protocol infusion vector (4). Thus, from $t_i$ to $t_m$ the method executions are stored in a memory and just at time $t_m$ a variant of the Cohen-Coon PID empirical adjustment method is applied and at that instant the switching system (23) the anesthetic drug infusion vector (5) is the result of the SynPID control system 24 according to the automatic infusion vector (22). The gains relating to the proportional gain matrix [5.19] are related to the patient's weight and the manual protocol infusion vector (4) are related to the patient's weight, height, gender and muscle mass.

Equation 14 involves all the steps defined for the proposed invention, but directly involves especially steps 3, 5 and 6. Once the gains in time $t_m$ have been calculated, they will remain constant until the recovery time $t_r$.

The systems that need adjustment are:

Filter bank (9): it is necessary to adjust the three parameters that refer to the cutoff frequency.

Multivariable controller with MIMO-PID synergy (16): it is necessary to adjust 18 parameters, for each SISO-PID controller a proportional, an integral and a derivative gain must be adjusted.

Infusion correction system (17): which uses the proportional gains of the MIMO-PID multivariable and synergistic controller (16).

| Ref. | Mathematical Definition | Eq. |
|---|---|---|
| 9 | $f_c = [f_1 \quad f_2 \quad f_3]^T$ | [3.3] |
| 9 | $f_c + \dfrac{N}{T_D}$ | [3.4] |
| 16 | $[K_P] = \begin{bmatrix} K_{P11} & K_{P12} & \ldots & K_{P1r} \\ K_{P21} & K_{P22} & \ldots & K_{P2r} \\ \vdots & \vdots & \ddots & \vdots \\ K_{Ps1} & K_{Ps2} & \ldots & K_{Psr} \end{bmatrix} = \begin{bmatrix} K_{P1} \\ K_{P2} \\ \vdots \\ K_{Ps} \end{bmatrix}$ | [5.4] |
| 16 | $[K_I] = \begin{bmatrix} K_{I11} & K_{I12} & \ldots & K_{I1r} \\ K_{I21} & K_{I22} & \ldots & K_{I2r} \\ \vdots & \vdots & \ddots & \vdots \\ K_{Is1} & K_{Is2} & \ldots & K_{Isr} \end{bmatrix} = \begin{bmatrix} K_{I1} \\ K_{I2} \\ \vdots \\ K_{Is} \end{bmatrix}$ | [5.5] |

-continued

| Ref. | Mathematical Definition | Eq. |
|------|------------------------|-----|
| 16 | $$[K_D] = \begin{bmatrix} K_{D11} & K_{D12} & \cdots & K_{D1r} \\ K_{D21} & K_{D22} & \cdots & K_{D2r} \\ \vdots & \vdots & \ddots & \vdots \\ K_{Ds1} & K_{Ds2} & \cdots & K_{Dsr} \end{bmatrix} = \begin{bmatrix} K_{D1} \\ K_{D2} \\ \vdots \\ K_{Ds} \end{bmatrix}$$ | [5.6] |
| 24 | $$SYN = \begin{bmatrix} S_{11} & S_{12} & S_{13} \\ S_{21} & S_{22} & S_{23} \\ S_{31} & S_{32} & S_{33} \end{bmatrix}^T = \begin{bmatrix} S_1 \\ S_2 \\ S_3 \end{bmatrix}^T$$ | [5.10] |
| | $K_P = W^{-1} \cdot K$ <br> $K_I = T_I^{-1} \times K_P$ <br> $K_D = K_P \times T_D$ <br> $T_I = \mathrm{diag}([T_I])$ <br> $T_D = \mathrm{diag}([T_D])$ | |

Ref. indicates the number that appears in the figures; Eq. indicates the equation of the general description where it has been defined, particularized for s = r = 3. "x" identifies the product element by element (Schur product).

Where K is a Universal Gain [(µg/(min))/UM]; [$K_P$] is the Proportional Gain Matrix [(m/(min kg))/UM]; [$K_I$] is the Integral Gain Matrix [(µg (min kg))/UM min)]; [$T_I$] is the integral action time matrix [min]; [$K_D$] is the derivative gain matrix [(m/kg)/UM]; [$T_D$] is the derivative action time matrix [min].

Equation 15: Adjustment of other parameters of the SynPID control system that are universal and common to all patients (common to inter/intra-patient variability). These parameters are generally constant, but can be explicitly and generally adjusted by sex, population groups (diabetics, obese persons . . . ), types of surgery, territories and/or ages.

Below are the parameters considered and the equations in which they appear:

| Para-meter | Type | Definition | Eq. Eq. |
|-----------|------|-----------|---------|
| W | Scalar | Patient Weight | [2.4] |
| $T_s$ | Scalar | Method execution period | [2.4] |
| $y_T$ | Vector | Objectives on the monitors <br> $y_T = [50 \quad 30 \quad 10]^T$ | [2.6] |
| D | Vector | Boluses per unit of mass <br> $D = [700 \quad 0.5 \quad 500]^T$; (µg/kg) | [2.4] |
| R | Vector | Constant induction infusion <br> $R = [100 \quad 0.3 \quad 2000]^T$; (µg/(kg · min)) | [2.5] |
| P | Vector | Decreased infusion in IPh <br> $\square = [3.2 \quad 0.69 \quad 0]^\square$; ((ng/(kg min))/s) | [2.5] |
| N | Scalar | PID filtering coefficient <br> N = 12 | [3.4] |
| $y_{thb}$ | Vector | Thresholds determining the maximum value of p <br> $y_{thb} = [40 \quad 20 \quad 0]^T$ | [4.4] |
| $y_{thg}$ | Vector | Thresholds determining the maximum value of y <br> $y_{thg} = [45 \quad 25 \quad 5]_T$ | [4.6] |
| [SYN] | Matrix | Drug synergy <br> $$[SYN] = \begin{bmatrix} 1 & 1 & 0 \\ 1 & 1 & 0 \\ 0 & 0 & 1 \end{bmatrix}^T$$ | [5.10] |
| $y_{HI}$ | Vector | Upper thresholds for the activation of the correction <br> $y_{HI} = [60 \quad 40 \quad 20]^T$ | [6.3] |
| $y_{LO}$ | Vector | lower thresholds for the activation of the correction <br> $y_{LO} = [40 \quad 20 \quad 0]^T$ | [6.4] |
| $u_{HI}$ | Vector | Upper infusion limits <br> $u_{HI} = [100 \quad 0.3 \quad 2000]^T$; (µg/(kg · min)) | [7.3] |
| $u_{LO}$ | Vector | Lower infusion limits <br> $u_{LO} = [0 \quad 0 \quad 0]^T$; (µg/(kg · min)) | [7.4] |

-continued

| Para-meter | Type | Definition | Eq. Eq. |
|-----------|------|-----------|---------|
| $u_{min}$ | Vector | Pump Resolutions <br> $u_{mn} = [u_{mn1} \quad u_{mn2} \quad u_{mn3}]^T$; (µg/(kg · min)) <br> Hardware dependent | [8.3] |
| $t_i$ | Scalar | IPh Start Time | [9.2] |
| $t_m$ | Scalar | MPh Start Time | [9.2] |
| $t_r$ | Scalar | RPh Start Time | [9.2] |

Industrial Application

Regarding the implementation of the multi-infusion drug system with synergy by control in CL MIMO-PID (SynPID) applied in IV anesthetic acts of the present invention, one of the embodiments contemplates its execution in code interpretable by Android, IOS, Arduino, Raspberry-PI devices, personal computers, commercial infusion pumps or specific hardware.

The SynPID control system runs iteratively every $T_s$ seconds and consists of the following phases: 1) Startup at $t_j$ where there are $N_j$ iterations of the method; 2) IPh, from $t_i$ to $t_m$, where there are $N_m$-$N_i$ iterations of the method; 3) MPh, from $t_m$ to $t_r$, and 4) RPh, from $t_r$, where there are $N_r$-$N_m$ iterations of the method. The result of each iteration is to obtain the anesthetic drug infusion vector (5) to be administered to the patient (1) with the infusion pump system (2) so that the monitoring variables vector (6) is led to the target vector of the monitored variables (8) despite the vector of surgical actions (7).

The actions to be taken in each of the phases of application of the SynPID method implemented in any of the aforementioned devices are:

1) Before startup, the following data must be obtained: 1) of the patient (1), the weight, age, sex, height and muscle mass to adjust the manual protocol infusion vector (4) from which the values will be derived of the vectors of equations [2.4] and [2.5]; 2) of the infusion pump system (2) its resolution to adjust the vector of the equation [8.3]; 3) of the SynPID system (24) its execution period shown in equation [2.4]; the drug synergy matrix shown in equation [5.10]; the asymmetry matrices of the control errors shown in equations [4.3] and [4.5] and in general of all the parameters shown in equation 15.

2) In the IPh the anesthetic drug infusion vector (5) that is administered to the patient (1) corresponds to the manual protocol infusion vector (4) as shown in equation [2.3], 3) At the end of the IPh, the adjustment is carried out of the gain matrices shown in equations [5.4], [5.5] and [5.6] and in general of all the parameters shown in equation 14.

4) In MPh, the anesthetic drug infusion vector (5) administered to the patient (1) corresponds to the automatic infusion vector (22).

5) In RPh the anesthetic drug infusion vector (5) that is administered to the patient (1) is annulled.

In an indeterminate Iteration of the SynPID control system, the following actions must be followed in the given order:

1. Start by acquiring the information of the monitoring variables vector (6) using the monitoring equipment (3), the information acquired in the current iteration and in the past iterations are stored in a memory for later use; the information obtained in this action will serve for the feedback of the control system in CL;

2. The target vector of the monitored variables must be set (8); the result of the current iteration and the past iterations are stored in a memory for later use;

3. Noise and artifacts from the monitoring variable vector (6) must be cleaned by means of a filter bank (9) to obtain the monitoring filtered variable vector (10); the result of the current iteration and the past iterations are stored in a memory for later use;

4. The control error vectors (12, 13, 14) must be calculated by means of a control error generator (11); each control error vector is formed by a proportional asymmetric error, an integral symmetric error and a derivative asymmetric error; using the current instants of the target vector of the monitored variables (8) and of the filtered monitoring variables vector (10); the result of the current iteration and of the past iterations are stored in a memory for later use;

5. The control infusion vector (15) must be calculated by means of a multivariable controller with MIMO-PID synergy (16) that has as inputs the control error vectors (12, 13, 14) and the manual protocol infusion vector (4); from each SISO-PID controller the contribution to each drug of each control error distributed in a proportional action that makes use of the current iteration, an integral action that makes use of the current iteration and all the past ones and a derivative action that makes use of the current iteration and the previous one is obtained; the result of the current iteration and of the past iterations are stored in a memory for later use;

6. A correction vector (18) must be calculated by means of an infusion correction system (17) that presents at its input the filtered monitoring variables vector (10) of the current Iteration; the result of the current iteration and of the past iterations are stored in a memory for later use;

7. A reliable control vector (20) must be calculated by means of a security system (19) that presents at its input the current Iteration of the control infusion vector (15) and the correction vector (18); the result of the current Iteration and the past Iterations are stored in a memory for later use;

8. A vector of automatic infusions (22) must be calculated by means of a quantification system (21) that presents at its input the current iteration of the reliable control vector (20); the result of the current iteration and the past iterations are stored in a memory for later use;

9. The anaesthetic drug infusion vector (5) must be defined by means of a switching system (23) that has as inputs the current iteration of the control infusion vector (15), of the manual protocol infusion vector (4) and of a zero vector; the result of the current iteration and of the past iterations are stored in a memory for later use;

10. Once the anesthetic drug infusion vector (5) has been obtained, a new iteration begins, returning to point one of this list and increasing the number of the iteration.

The multi-infusion system of anesthetic drugs with synergy by control in CL MIMO-PID (SynPID) applied in IV anesthetic acts of the present invention, is prepared for installation in intelligent infusion pumps that make use of an electronic circuit based on a microprocessor with memory, configured to determine the anesthetic drug infusion vector (5) to administer to the patient (1) by IV in a surgical act; each iteration period Lis configurable between 1 and 30 seconds. The mission of the anesthetic drug infusion vector (5) is to obtain a satisfactory anesthetic state given by the target vector of the monitored variables (8).

The SynPID control system is configured to carry out the method presented in the invention that is repeated every $T_s$ seconds, where the system comprises executing the following blocks:

1. Memory: Memorization of the data history of the information from the monitoring equipment (3), the target vector of the monitored variables (8), filtered monitoring variables vector (10), vectors of control errors (12, 13, 14), vector of control infusions (15), correction vector (18), reliable control vector (20) and anesthetic drug infusion vector (5) performed by the infusion pump system (2) and the computer code based on the instructions necessary to execute the SynPID method in a processor;

2. Counter: An electronic time counter for determining the phases IPh, MPh and RPh, estimating that IPh lasts between 5 and 10 minutes, that MPh is very variable in duration depending on the surgery and that RPh lasts between 10 and 20 minutes; this counter implements the switching system (23) in the form of computer code and the relevant instructions to execute them in the processor;

3. Adjustment: A software routine that is executed at time $t_m$ to adjust the parameters of the SynPID control system to each patient (1) using the actions shown in equation 14 and the system memory;

4. Routine 1: Reusable software routine for the implementation of the filter bank (9) using the gain matrix $[K_D]$ shown in equation [5.6] and the filtering coefficient N presented in equation [3.4]; the routine can be executed several times with modifiable input parameters, the routine makes use of the information stored in the memory;

5. Routine 2: Reusable software routine for the implementation of the control error generator (11) making use of the elements of the matrices [B] and [G] given in equations [4.3] and [4.5], whose values are between 1 and 2; a single routine is implemented with the code for obtaining the control error vectors (12, 13, 14), the routine can be executed several times with modifiable input parameters, the routine makes use of the information stored in the memory;

6. Routine 3: Reusable software routine for the implementation of the multivariable and synergistic MIMO-PID controller (16) using the SISO-PID controllers defined in equations [5.14] and [5.15]; a single routine is implemented with the execution code of the SISO-PID controllers that form the three MISO-PID control subsystems (25, 26, 27) and that in turn form the multivariable controller and with MIMO-PID synergy (16), the routine can be executed several times with modifiable input parameters, the routine makes use of the information stored in the memory;

7. Routine 4: Software routine that calculates the control infusion vector (15) with the results obtained by applying Routine 3 relating to the results of the SISO-PID controllers and the manual protocol infusion vector (4), shown in the equations [5.14] and [2.4] [2.5]; a single routine is implemented with the execution code to obtain the control infusion vector (15), the routine makes use of the information stored in the memory;

8. Routine 5: Reusable software routine for the implementation of the infusion correction system (17) making use of the filtered monitoring variables vector (10) shown in equation [3.2], making use of the cut-off frequencies defined in equations [3.3] and [3.4]; a single routine is implemented with the execution code of the infusion correcting system (17), the routine can be executed several times with modifiable input parameters; the routine makes use of the Information stored in the memory;

9. Routine 6: Reusable software routine for the implementation of the security system (19) making use of the control infusion vector (15) shown in equations [6.1] and [6.2], a single routine is implemented with the execution code of the security system (19), the routine can be executed several times with modifiable input parameters; the routine makes use of the information stored in the memory;

10. Routine 7: Reusable software routine for the implementation of the quantification system (21) making use of the reliable control vector (20) shown in equations [7.1] and [7.2], a single routine is implemented with the execution code of the quantification system (21); the routine can be executed several times with modifiable input parameters; the routine makes use of the Information stored in the memory.

The invention claimed is:

1. A closed-loop system for intravenous automatic multi-infusion of anaesthetic drugs with synergy to patients, the system comprising:

an infusion pump subsystem configured to deliver to a patient a number of drugs;

a monitoring subsystem configured to measure a set of physiological variables with patient status information;

a control subsystem configured to adapt an amount delivered of each drug by the infusion pump subsystem, based on a predetermined initial infusion amount, monitoring target values, a feedback of the measured physiological variables and a multivariable controller with multiple input and multiple output-proportional, integral and derivative (MIMO-PID) synergy between the drugs, wherein the control subsystem comprises:

a control error generating module configured to calculate errors based on the monitoring target values and the feedback of the measured physiological variables;

a controller configured to determine a control infusion for each of the drugs based on the errors calculated by the control error generating module and the predetermined initial infusion amount;

a correction module configured to receive the measurements of the set of physiological variables from the monitoring subsystem and modify the control infusion of the controller, increasing said infusion as a function of an upper threshold or decreasing it as a function of a lower threshold, to set the physiological variables at a preset safe range for the physiological variables;

a safety module configured to receive the control infusion of each drug and modify said infusion by limiting it between two infusion values, a lower limit and an upper limit, which ensure there is no over-medication for each drug;

the control error generating module being configured to generate, for each of the variables of the set of physiological variables with patient status information to be measured by the monitoring subsystem, a control vector and wherein the controller comprises a multiple input single output (MISO) control subsystem for each drug, which in turn comprises single input single output (SISO) controllers configured to receive the control errors and determine a control infusion vector for each drug;

the control subsystem being customized specifically for the patient based on methods of tuning the controller through various gains relative to each SISO controller and at least one physiological parameter specific to the patient including weight, height, sex, muscle mass or clinical history, each MISO control subsystem is multiple input single output control-proportional, integral and derivative control subsystem (MISO-PID), and the SISO controllers include single input single output-proportional, integral and derivative (SISO-PID); and the control vector of the control error generating module, having a proportional asymmetric error component, an integral symmetric error component, a derivative asymmetric error component and additional error components, and wherein SISO-PIDs are configured to respectively receive the proportional asymmetric error component, the integral symmetric error component and the derivative asymmetric error component of each control vector and determine the control infusion vector for each drug.

2. The system according to claim 1 further comprising:

a quantification module connected between the safety module and the infusion pump subsystem, wherein the quantification module is configured to adapt the output vector of the safety module so as to be interpretable by the infusion pumps.

3. The system according to claim 1, wherein the control subsystem further comprises:

a filter bank configured to receive feedback signals sent by the monitoring subsystem.

4. The system according to claim 1, wherein the control error generating module comprises several error generating sub-modules for each of the variables of the set of variables monitored with patient status information to be measured by the monitoring subsystem.

5. The system according to claim 1, wherein the drugs are anesthetic drugs that induce the patient to an anesthetic state and wherein the set of physiological variables that measures the monitoring subsystem have information on said anesthetic state of the patient.

6. The system of claim 5, wherein the set of variables with patient anesthetic status information comprises a bispectral index, a noxious stimulation response index, and neuromuscular blockade index.

7. The system according to claim 6 wherein the infusion pump subsystem comprises: a first infusion pump of a drug with hypnotic properties, a second infusion pump of a drug with analgesic properties and a third infusion pump of a drug with muscle relaxation properties.

8. The system according to claim 7 wherein the drug with hypnotic properties is propofol, the drug with analgesic properties is remifentanil and the drug with muscle relaxation properties is rocuronium.

9. The system according to claim 7, further comprising additional pumps for the infusion of other drugs that alter the anesthetic state or vital signs of the patient.

10. The system according to claim 1 wherein the control subsystem is further configured for glucose control of type 1 diabetes patients, wherein the monitoring subsystem is further configured for measuring the glucose of the patient, and wherein the infusion subsystem is further configured for delivering to the patient a continuous and controlled amount of insulin and glucagon.

* * * * *